(12) United States Patent  (10) Patent No.: US 7,634,937 B2
Burdett et al.  (45) Date of Patent: Dec. 22, 2009

(54) SYSTEMS AND METHODS FOR MONITORING SOLIDS USING MECHANICAL RESONATOR

(75) Inventors: Ian Burdett, Charleston, WV (US); Timothy Lynn, Glen Gardner, NJ (US); Oleg Kolosov, San Jose, CA (US); Daniel Paul Zilker, Jr., Charleston, WV (US); Leonid Matsiev, San Jose, CA (US)

(73) Assignee: Symyx Solutions, Inc., Sunnyvale, CA (US)

( * ) Notice: Subject to any disclaimer, the term of this patent is extended or adjusted under 35 U.S.C. 154(b) by 764 days.

(21) Appl. No.: 11/296,597

(22) Filed: Dec. 6, 2005

(65) Prior Publication Data

US 2007/0003450 A1    Jan. 4, 2007

Related U.S. Application Data

(60) Provisional application No. 60/696,444, filed on Jul. 1, 2005.

(51) Int. Cl.
*G01N 19/00* (2006.01)
*G01N 33/44* (2006.01)
*C08F 2/34* (2006.01)

(52) U.S. Cl. .............. 73/24.06; 73/24.01; 422/68.1; 700/269; 702/24

(58) Field of Classification Search .......... 73/24.01, 73/290, 597, 628, 24.06; 422/68.1; 702/24; 700/269
See application file for complete search history.

(56) References Cited

U.S. PATENT DOCUMENTS

| | | | |
|---|---|---|---|
| 3,999,421 A | 12/1976 | Creswick | 73/32 |
| 4,466,989 A | 8/1984 | Haller et al. | 427/185 |
| 4,543,399 A | 9/1985 | Jenkins, III et al. | 526/70 |
| 4,588,790 A | 5/1986 | Jenkins, III et al. | 526/67 |
| 4,858,144 A | 8/1989 | Marsaly et al. | 364/496 |
| 4,993,264 A | 2/1991 | Cody et al. | 73/579 |
| 5,028,670 A | 7/1991 | Chinh et al. | 526/73 |
| 5,148,405 A | 9/1992 | Belchamber et al. | 367/13 |
| 5,317,036 A | 5/1994 | Brady, III et al. | 523/223 |
| 5,352,749 A | 10/1994 | DeChellis et al. | 526/68 |
| 5,405,922 A | 4/1995 | DeChellis et al. | 526/68 |
| 5,408,882 A | 4/1995 | McKinley et al. | 73/597 |
| 5,435,972 A | 7/1995 | Daw et al. | 422/108 |
| 5,436,304 A | 7/1995 | Griffin et al. | 526/68 |

(Continued)

FOREIGN PATENT DOCUMENTS

CA    2178238    12/1997

(Continued)

OTHER PUBLICATIONS

International Search Report and Written Opinion from PCT Application No. PCT/US06/25385 mailed Nov. 13, 2007.

(Continued)

*Primary Examiner*—Fred M Teskin
(74) *Attorney, Agent, or Firm*—Zilka-Kotab, PC

(57) ABSTRACT

Particle and multi-phase system monitoring methods, systems and apparatus are disclosed. Preferred embodiments comprise one or more mechanical resonator sensing elements. In preferred embodiments a sensor or a sensor subassembly is ported to a fluidized bed vessel such as a fluidized bed polymerization reactor.

77 Claims, 16 Drawing Sheets

U.S. PATENT DOCUMENTS

| | | | |
|---|---|---|---|
| 5,453,471 A | 9/1995 | Bernier et al. | 526/68 |
| 5,462,999 A | 10/1995 | Griffin et al. | 526/68 |
| 5,586,445 A | 12/1996 | Bessler | 62/126 |
| 5,616,661 A | 4/1997 | Eisinger et al. | 526/88 |
| 5,627,242 A | 5/1997 | Jacobsen et al. | 526/60 |
| 5,665,818 A | 9/1997 | Tilston et al. | 525/53 |
| 5,668,228 A | 9/1997 | Chinh et al. | 526/67 |
| 5,677,375 A | 10/1997 | Rifi et al. | 525/53 |
| 5,708,191 A | 1/1998 | Greenwood et al. | 73/32 |
| 5,741,961 A | 4/1998 | Martin et al. | 73/32 |
| 5,886,250 A | 3/1999 | Greenwood et al. | 73/32 |
| 5,969,236 A | 10/1999 | Hirota et al. | 73/61.75 |
| 5,987,972 A | 11/1999 | Hirota et al. | 73/61.75 |
| 6,030,917 A | 2/2000 | Weinberg et al. | 502/104 |
| 6,055,873 A | 5/2000 | Adams | 73/865.5 |
| 6,082,180 A | 7/2000 | Greenwood | 73/32 |
| 6,082,181 A | 7/2000 | Greenwood | 73/32 |
| 6,182,499 B1 | 2/2001 | McFarland et al. | 73/24.06 |
| 6,223,589 B1 | 5/2001 | Dickert et al. | 73/61.45 |
| 6,301,546 B1 | 10/2001 | Weinstein et al. | 702/23 |
| 6,311,549 B1 | 11/2001 | Thundat et al. | 73/54.24 |
| 6,336,353 B2 | 1/2002 | Matsiev et al. | 73/24.06 |
| 6,383,553 B1 | 5/2002 | Tondar et al. | 427/8 |
| 6,384,157 B1 | 5/2002 | Cai et al. | 526/88 |
| 6,393,895 B1 | 5/2002 | Matsiev et al. | 73/24.06 |
| 6,401,519 B1 | 6/2002 | McFarland et al. | 763/24.6 |
| 6,414,093 B1 | 7/2002 | Takimiya et al. | 526/88 |
| 6,417,295 B1 | 7/2002 | Tamura et al. | 526/59 |
| 6,460,412 B1 | 10/2002 | Cai et al. | 73/290 |
| 6,494,079 B1 | 12/2002 | Matsiev et al. | 73/24.05 |
| 6,689,847 B2 | 2/2004 | Mawson et al. | 526/116 |
| 6,818,183 B2 | 11/2004 | Hajduk et al. | 422/68.1 |
| 6,873,916 B2 | 3/2005 | Kolosov et al. | 702/25 |
| 2001/0010174 A1 | 8/2001 | Matsiev et al. | 73/592 |
| 2002/0155036 A1 | 10/2002 | Hajduk et al. | 422/130 |
| 2002/0178805 A1 | 12/2002 | DiFoggio et al. | 73/152.55 |
| 2004/0099050 A1 | 5/2004 | Matsiev et al. | 73/61.45 |
| 2004/0244487 A1 | 12/2004 | Kolosov et al. | 73/570 |
| 2004/0250622 A1 | 12/2004 | Kolosov et al. | 73/570 |
| 2005/0166679 A1 | 8/2005 | Carlson et al. | 73/579 |
| 2005/0262944 A1 | 12/2005 | Bennett et al. | 73/592 |
| 2006/0031030 A1 | 2/2006 | Bennett et al. | 702/50 |

FOREIGN PATENT DOCUMENTS

| | | |
|---|---|---|
| EP | 0649992 | 8/1994 |
| EP | 0766086 | 4/1997 |
| EP | 0634421 | 10/1997 |
| EP | 0802202 | 10/1997 |
| EP | 0943091 | 5/2003 |
| JP | 581860142 | 10/1983 |
| JP | 6228961 | 8/1994 |
| JP | 06228961 | 8/1994 |
| JP | 21278904 | 10/2001 |
| JP | 2001278904 | 10/2001 |
| WO | WO 99/61485 | 12/1999 |
| WO | WO 9961485 | 12/1999 |
| WO | WO 01/94900 | 12/2001 |
| WO | WO 03/100390 | 12/2003 |
| WO | WO 2004/086020 | 10/2004 |

OTHER PUBLICATIONS

Bakker et al., "Design Reactors via CFD" Chemical Engineering Progress, Dec. 21, 2001, vol. 97, No. 12, pp. 30-39.

C.E.A. Finney et al., "Measuring Slugging Bed Dynamics with Acoustic Sensors" KONA: Powder and Particle Jun. 1, 1997.

F.A.N. Fernandes et al., "Fluidized Bed Reactors for Polythylene Production. The Influence of Polythylene Prepolymerization" Brazilian Journal of Chemical Engineering, Jun. 2000.

"Metallocene Catalysis Polymerization" Department of Polymer Science: University of Southern Mississippi, 1997.

Schouten et al., "Monitoring the Quality of Fluidization Using the Short-Term Predictability of Pressure Fluctuations" AIChE Journal, vol. 44, No. 1, Jan. 1998: 48-60.

"GranuMet XP Polymer: Detection of Entrained Powders in gas streams" Process Analysis and Automation Ltd. (2004) http://www.paa/co.uk/process/products/granumet/polymer.asp.

"Description" http://mindspring.com/~jonasinc/particle_m.htm, (2000).

"GranuMet XP Polymer: Detection of Condensates in recycle loops" Process Analysis and Automation Ltd. http://www.paa/co.uk/process/products/granumet/polymer.asp,(2004).

"MiniRanger Plus: The Advantages of Non-Contacting Ultrasonic Level Measurement Are Now Within Reach" Milltronics.

"Electrostatics" Progression, Inc. 2005 http://www/.progression-systems.com/solutionsmenu/electrostatics.htm.

"Particle System Characterization" Mettler Toledo http://us.mt.com/mt/filters/products-applications_ autochem_partilce-system-characterization, (2004).

PCT Patent Application No. PCT/US06/04231 which was filed on Feb. 3, 2006.

"Polythylene" Department of Polymer Science: University of Southern Mississippi, 1997.

"Zieger-Natta Vinyl Polymerization" Department of Polymer Science: University of Southern Mississippi, 1997.

TUNING FORK EQUIVALENT CIRCUIT, $Z_{tf}$ (11222)   READOUT INPUT IMPEDANCE, $Z_{in}$ (11224)

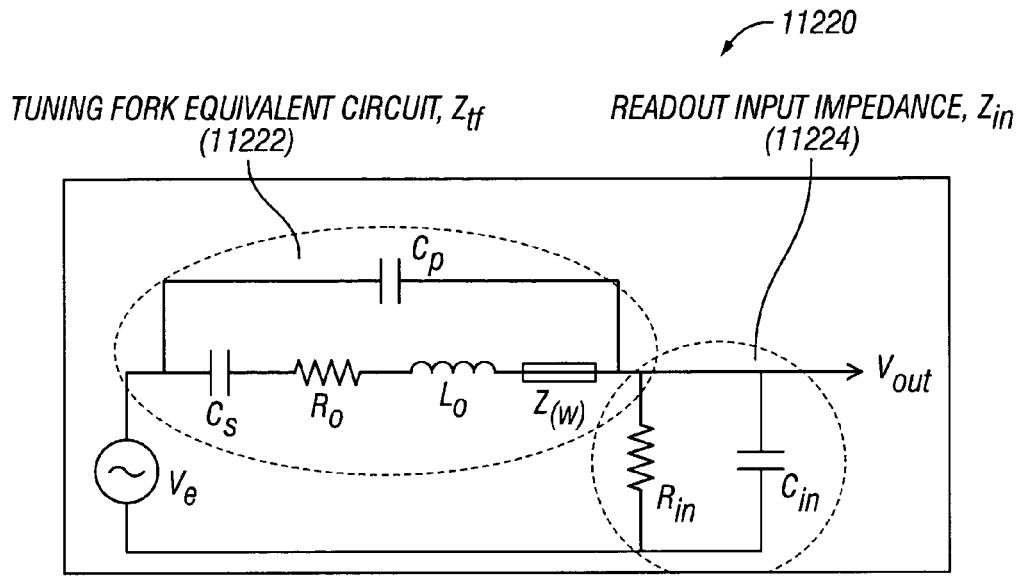

FIG. 8A

$V_{out}$ $(Co, Cp, Lo, Cs, Ro, Z(\omega), A, B, \rho, \eta, \omega, \varepsilon)$     (1)

$$V_{out}(\omega) = \frac{V_0(Z_{in}(\omega))}{(Z_{in}(\omega)) + (Z_{tf}(\omega))} \quad (2)$$

$$Z_{in} = R_{in} * (1/i\omega C_{in})(R_{in} + 1/i\omega C_{in})^{-1} \quad (3)$$

$$Z_{tf} = (1/i\omega Cp)(Ro + 1/i\omega Cs + i\omega Lo) \\ (1/i\omega Cp + Ro + 1/i\omega Cs + i\omega Lo)^{-1} \quad (4)$$

$$Z(\omega) = Ai\omega\rho + B*(\omega\rho\eta)^{1/2}(1+i) \quad (5)$$

$\varepsilon_{measured} = a + k*Cp\ (measured)$     (6)

$\varepsilon_{measured} = [\varepsilon_{cal} - (\varepsilon_{cal} - 1)*[Cpcal/(Cpcal - Cpo)]] +$
$[Cp(measured)*[(\varepsilon_{cal} - 1)/(Cpcal - Cpo(vacuum))]]$     (7)

$a = [\varepsilon_{cal} - (\varepsilon_{cal} - 1)*[Cpcal/(Cpcal - Cpo)]]$     (8)

$k = [(\varepsilon_{cal} - 1)/(Cpcal - Cpo(vacuum))]$     (9)

$Cp(measured)$ IS A FUNCTION OF "$k$"     (10)

FIG. 8B

$$Z(\omega) = Ai\omega\rho + B\sqrt{\omega\rho\eta}\,(1+i)$$

$$Z(\omega) = i\omega\Delta L + \Delta Z\sqrt{\omega}\,(1+i)$$

$$\Delta L = A\rho,\ \Delta Z = B\sqrt{\rho\eta}$$

SYSTEMS AND METHODS FOR MONITORING SOLIDS USING MECHANICAL RESONATOR

RELATED APPLICATIONS

This application claims priority to U.S. Provisional Patent Application Ser. No. 60/696,444 filed Jul. 1, 2005 with title "SYSTEMS AND METHODS FOR MONITORING SOLIDS USING MECHANICAL RESONATOR" and which is herein incorporated by reference.

BACKGROUND OF INVENTION

The present invention generally relates to the field of mechanical resonator sensors and methods and more particularly to the field of mechanical resonator sensors and methods for monitoring beds of particles and other multi-phase systems having particles. Such mechanical resonator sensors are suitable for implementation in fluidized bed systems including fluidized bed polymerization reactor systems for functions such as property characterization, process monitoring, and process control. The present invention relates, in preferred embodiments, to devices and methods adapted for use in open and/or closed fluidized bed systems such as fluidized bed polymerization reactor systems and related reaction and recirculating fluid systems (e.g., reaction chamber, velocity reduction zone, recycle line, etc.). The present invention relates, in particularly preferred embodiments, to the field of fluid sensor devices and methods involving a mechanical resonator sensor such as a flexural resonator sensor.

Effective approaches for measuring characteristics of fluids using mechanical resonators are disclosed in U.S. Pat. Nos. 6,401,519; 6,393,895; 6,336,353; 6,182,499; 6,494,079 and EP 0943091 B1, each of which are incorporated by reference herein for all purposes. See also, Matsiev, "*Application of Flexural Mechanical Resonators to Simultaneous Measurements of Liquid Density and Viscosity*," IEEE International Ultrasonics Symposium, Oct. 17-20, 1999, Lake Tahoe, Nev., which is also incorporated by reference herein for all purposes. The use of a quartz oscillator in a sensor has been described as well in U.S. Pat. Nos. 6,223,589 and 5,741,961, and in Hammond, et al., "*An Acoustic Automotive Engine Oil Quality Sensor*", Proceedings of the 1997 IEEE International Frequency Control Symposium, IEEE Catalog No. 97CH36016, pp. 72-80, May 28-30, 1997.

The use of other types of sensors is also known in the art. For example, the use of acoustic sensors has been addressed in applications such as viscosity measurement in J. W. Grate, et al, Anal. Chem. 65, 940A-948A (1993)); "*Viscosity and Density Sensing with Ultrasonic Plate Waves*", B. A. Martin, S. W. Wenzel, and R. M. White, Sensors and Actuators, A21-A23 (1990), 704-708; "*Preparation of chemically etched piezoelectric resonators for density meters and viscometers*", S. Trolier, Q. C. Xu, R. E. Newnham, Mat. Res. Bull. 22, 1267-74 (1987); "*On-line Sensor for Density and Viscosity Measurement of a Liquid or Slurry for Process Control in the Food Industry*", Margaret S. Greenwood, Ph.D. James R. Skorpik, Judith Ann Bamberger, P. E. Sixth Conference on Food Engineering, 1999 AIChE Annual Meeting, Dallas, Tex.; U.S. Pat. Nos. 5,708,191; 5,886,250; 6,082,180; 6,082,181; and 6,311,549; and "*Micromachined viscosity sensor for real-time polymerization monitoring*", O. Brand, J. M. English, S. A. Bidstrup, M. G. Allen, Transducers '97, 121-124 (1997). See also, U.S. Pat. No. 5,586,445 ("*Low Refrigerant Charge Detection Using a Combined Pressure/Temperature Sensor*").

Notwithstanding the above, there remains a need in the art for alternative or improved sensor devices and methods for efficiently evaluating particles and multi-phase systems containing particles in beds and fluidized bed systems, including for example in fluidized bed polymerization reactor systems. Examples in which such a need exists include those fluidized bed systems used in connection with the petroleum, chemical, pharmaceutical, healthcare, environmental, military, aerospace, construction, heating, ventilating, air-conditioning, refrigeration, food, and transportation industries. In particular, there remains a need in the art for a cost-effective approach for monitoring particle and fluidized bed dynamics and properties in fluidized bed polymerization reactor systems, such as the systems disclosed in U.S. Pat. Nos. 5,317,036 and 6,689,847, each of which is incorporated by reference herein for all purposes. Because fluidized bed systems are often closed, it is difficult to monitor definable parameters and changes in condition, e.g., how the bed and its components are presently behaving and reacting to process changes, the level of product in the vessel, etc. This in turn makes it difficult to anticipate problems such as fluidized bed collapse, agglomeration, and sheeting.

Fluidized bed collapse can generally have undesirable consequences. In a fluidized bed polymerization reactor system, fluidized bed collapse is a very costly occurrence, both in terms of production time lost, and often the need to physically remove agglomerations from the reactor system before the fluidized bed can be reinitiated. Thus, it would be desirable to detect, in situ, characteristics of the fluidized bed that could indicate a likelihood of bed collapse.

Another issue requiring attention is how to ensure uniform fluidization of the bed. Uniform fluidization in a fluidized bed polymerization reactor system is important for many reasons, among them reaction efficiency, and avoidance of overheating. Because polymerization reactions are typically exothermic, heat transfer out of the reactor is critical to avoid such things as particle agglomeration and runaway reactions. Non-uniform fluidization of the bed can create "hot spots," which in turn can cause the newly-formed polymer particles to become tacky due to elevated temperatures. The tackiness can cause particle agglomeration, and more devastatingly, sheeting. In agglomeration, the particles stick together, forming agglomerated particles that affect fluid flow and may be difficult to remove from the system. In sheeting, the tacky particles gather on a surface of the reactor system, such as the wall of the reactor vessel, forming a sheet of polymer particles. Sheeting is particularly malicious in that a sheet falling from the reactor wall can damage system components such as sensors as well as disrupt fluid flow resulting in collapse of the fluidized bed. When sheeting is finally detected, often after the damage is done, the reactor system must be stopped and the sheeting physically removed. Again, the lost production time is very costly. Thermocouples are used as sensors in the fluidized bed polymerization industry and are effective at detecting the local temperature of a gas flowing near the reactor wall, however, they provide very little indication of a uniformity of the bed. Nor do they provide any indication of a tackiness of the particles or if sheeting is occurring. Thus, it would be desirable to detect, in situ, characteristics of the fluidized bed and/or particles therein that could indicate a uniformity of the bed as well as provide an early indication of a likelihood or occurrence of particle agglomeration and sheeting.

SUMMARY OF INVENTION

It is therefore an object of the present invention to provide improved sensor devices and methods for efficiently monitoring or characterizing particles and multi-phase systems containing the same in beds and fluidized bed systems. In particular, it is an object of the invention to provide a cost-effective approach for monitoring both fluidized and nonfluidized systems (e.g., fluidized beds and static beds of particles, such as polymer particles). In preferred embodiments, it is an object of the invention to provide devices and methods for monitoring particles in a fluidized bed polymerization reactor system.

Briefly, therefore, the present invention is broadly directed to various methods for monitoring particles or multi-phase systems containing particles (e.g., for monitoring a property of particles or multi-phase systems) in a fluidized and non-fluidized bed system using a sensor, such as a mechanical resonator sensor. In preferred embodiments, the sensor is a flexural resonator sensor. Based on a monitored response of the mechanical resonator, a localized density, a granular temperature, a mixing factor, and/or an elastic modulus of the particles or multi-phase system can be characterized or determined.

The invention is also broadly directed to various systems for monitoring a property of one or more particles in one or more fluidized or nonfluidized systems, and in preferred embodiments, in polymerization reactor systems. The system generally comprises at least one sensor within a fluidized bed system, such as a mechanical resonator sensor within a fluidized bed system. In preferred embodiments, the sensor is a flexural resonator sensor, and more preferably, a tuning fork sensor. The system also comprises one or more circuits, such as signal processing circuits and/or data retrieval circuits.

The invention is further broadly directed to various apparatus for use in monitoring a property of one or more particles or multi-phase systems in fluidized or nonfluidized systems, which preferably include solids in a gaseous continuous phase. In preferred embodiments, the unit includes a flexural resonator sensor or flexural resonator sensor subassembly.

In the methods, systems and apparatus of the present invention, a property of particles or multi-phase systems in a fluidized or nonfluidized system is monitored using a mechanical resonator. In each case, the sensor is preferably a mechanical resonator sensor, and is most preferably a flexural resonator sensor. In preferred embodiments, a flexural resonator sensor comprises a flexural resonator sensing element having a sensing surface for contacting the particles or multi-phase system being sensed. In operation during a sensing period, the sensing surface of a flexural resonator contacts the particles being sensed. The flexural resonator sensor can be operated passively or actively, and if actively operated, is preferably excited using a stimulus signal. The particular nature of the stimulus signal is not critical, but in some embodiments, the stimulus signal can be a waveform having a frequency (e.g., a predetermined frequency) or having a range of frequencies (e.g., being swept over a determined or predetermined range of frequencies), and in each such case, having a frequency or a range of frequencies of less than about 1 MHz. In some embodiments, additional sensors (e.g., such as temperature and/or pressure sensors) can be employed in combination with a mechanical resonator sensor such as a flexural resonator sensor. Further discussion of preferred sensors and sensor subassemblies (comprising or more components of a sensor), as well as the preferred use thereof, are described hereinafter.

General Overview—Methods

Generally, a method for monitoring fluidized polymer particles in a fluidized bed polymerization reactor system comprises polymerizing a gaseous monomer in a fluidized bed polymerization reactor of the system thereby forming fluidized polymer particles in the fluidized bed polymerization reactor, contacting a mechanical resonator with the fluidized polymer particles in the reactor system, and monitoring a response of the mechanical resonator.

In another embodiment, a method for monitoring a bed of polymer particles comprises contacting a mechanical resonator with polymer particles in the bed of polymer particles, the bed further comprising a gaseous fluid in interstitial spaces defined between the polymer particles, stimulating the mechanical resonator to generate a response of the mechanical resonator, and monitoring the response of the mechanical resonator.

In a further embodiment, a method for monitoring fluidized particles comprises fluidizing particles to form a multi-phase system comprising the fluidized particles and a gaseous continuous phase, contacting a mechanical resonator with the fluidized particles, stimulating the mechanical resonator to generate a response of the mechanical resonator, monitoring the response of the mechanical resonator, and characterizing the multi-phase system by determining at least one of (i) a localized density, (ii) a granular temperature, and (iii) a mixing factor, in each case based on the monitored response of the mechanical resonator.

In yet another embodiment, a method for determining an elastic modulus of particles in a multi-phase system comprises contacting a mechanical resonator with particles, stimulating the mechanical resonator to generate a response of the mechanical resonator, monitoring the response of the mechanical resonator, and determining an elastic modulus of the particles based on the monitored response of the mechanical resonator.

In another embodiment, a method for monitoring a polymerization reaction in a fluidized bed polymerization reactor system comprises polymerizing a gaseous monomer in a fluidized bed polymerization reactor of the system thereby forming fluidized polymer particles in the fluidized bed polymerization reactor, monitoring the fluidized polymer particles in the reactor system using a sensor comprising a mechanical resonator, and determining, based on a monitored response of the sensor, at least one of (i) an occurrence or extent of agglomeration of the fluidized polymer particles in the system, (ii) an occurrence or extent of polymer sheeting in the system, (iii) a rate of polymerizing in the fluidized bed polymerization reactor, (iv) a level of condensed liquid in the fluidized bed polymerization reactor, (v) an occurrence or extent of channeling of the fluidized polymer particles in the system, (vi) an occurrence or extent of fluidization of the polymer particles in the system, and (vii) an occurrence or extent of plugging of a gas distribution plate in the system.

In a further embodiment, a method for controlling a process condition in a fluidized bed polymerization reactor system comprises polymerizing a gaseous monomer in a fluidized bed polymerization reactor of the system under a set of process conditions to form fluidized polymer particles in the reactor, monitoring a response of a sensor in the fluidized bed polymerization reactor system over a period of time, wherein the sensor comprises a mechanical resonator, and varying at least one process condition of the set based on a monitored output signal of the sensor.

General Overview—Systems and Apparatus

In the systems or apparatus of the invention, a fluidized bed polymerization reactor system comprises a reactor vessel having an inlet port, the inlet port being adapted for receiving a gaseous fluid for fluidizing polymer particles in the reactor vessel, and a sensor comprising a mechanical resonator, the mechanical resonator comprising a sensing surface adapted for exposure to the fluidized polymer particles within the reactor system.

In another embodiment, an apparatus comprising a sensor for use in monitoring fluidized particles includes a flexural resonator having a sensing surface adapted for exposure to a multi-phase system comprising fluidized particles in at least one of a gaseous continuous phase and a liquid phase, and a signal processing circuit in electrical communication with the flexural resonator for receiving an output signal from the flexural resonator during a sensing period, the signal processing circuit configured for processing the received signal to generate data representing at least one of localized density of the fluidized particles, granular temperature of the fluidized particles, mixing factor of the fluidized particles and combinations thereof.

The present invention offers significant advantages over previously-known approaches for monitoring particles in fluidized and nonfluidized systems, especially in systems such as fluidized bed polymerization reactor systems where monitoring is difficult. In particular, the invention offers substantial flexibility to configure devices and methods that are efficient, effective and affordable for generating data associated with one or more properties of particles and multi-phase systems containing particles, and thereby providing a more comprehensive dataset from which process control and/or servicing decisions can be made. This flexibility allows for applications of the devices and methods of the invention across diverse industries, including for example, across industries such as the petroleum, chemical, pharmaceutical, healthcare, environmental, military, aerospace, construction, heating, ventilating, air-conditioning, refrigeration, food, and transportation industries.

Other features, objects and advantages of the present invention will be in part apparent to those skilled in art and in part pointed out hereinafter. All references cited in the instant specification are incorporated by reference for all purposes. Moreover, as the patent and non-patent literature relating to the subject matter disclosed and/or claimed herein is substantial, many relevant references are available to a skilled artisan that will provide further instruction with respect to such subject matter.

BRIEF DESCRIPTION OF THE DRAWINGS

FIGS. 8A through 8F are schematic representations of equivalent circuits for a sensor comprising a flexural resonator sensing element (FIGS. 8A, 8D, 8E, and 8F) and of equations relating thereto (FIG. 8B and FIG. 8C).

The invention is described in further detail below with reference to the figures, in which like items are numbered the same in the several figures.

DETAILED DESCRIPTION OF THE INVENTION

The following paragraphs describe certain features and combinations of features that can be used in connection with each of the methods, systems and apparatus of the invention, as generally described above. Also, particular features described hereinafter can be used in combination with other described features in each of the various possible combinations and permutations. As such, the invention is not limited to the specifically described embodiments.

Preferred General Methods

Figure 1:
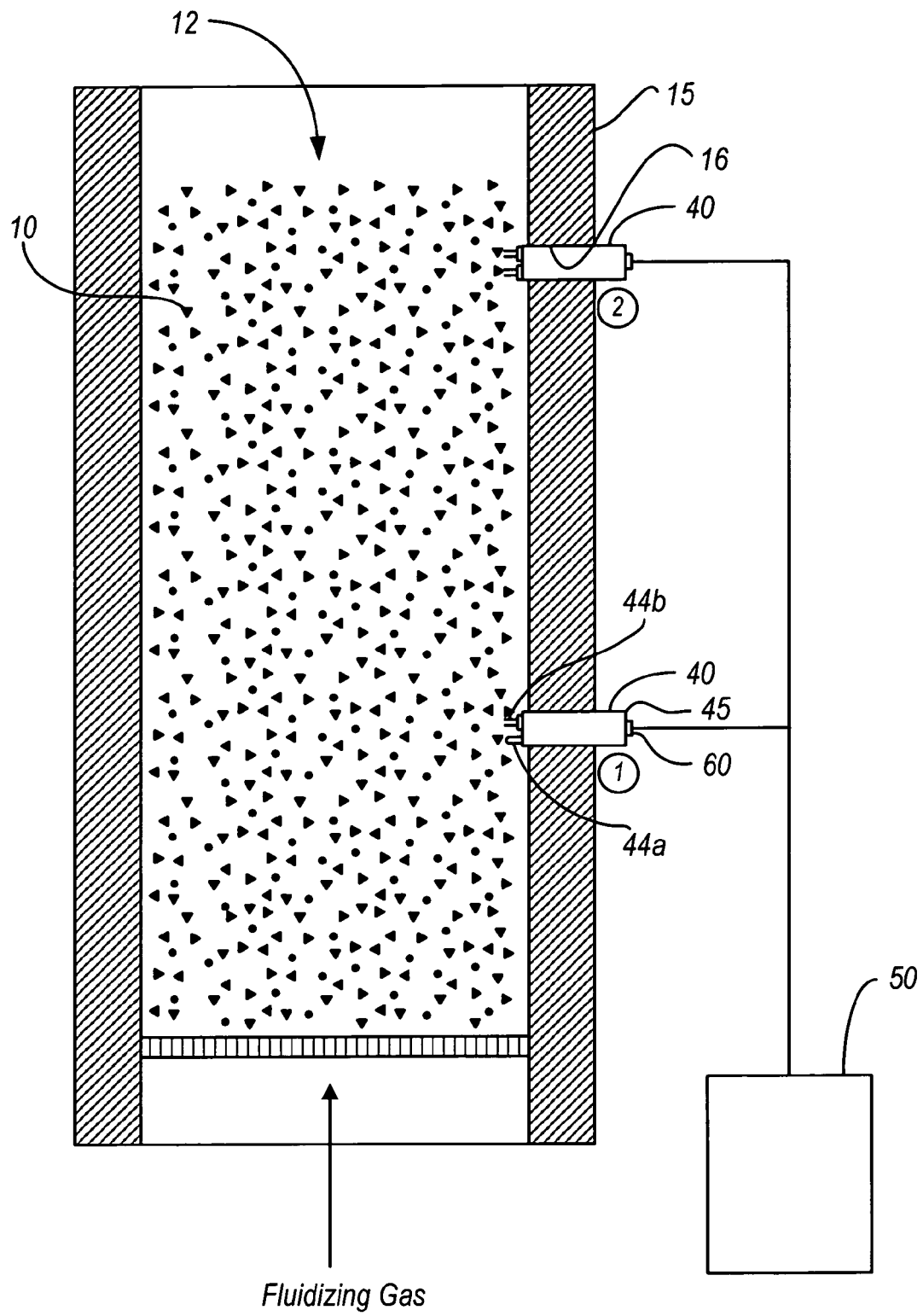
FIG. 1 is a schematic representation of the general methods, systems and/or apparatus of the invention.

A preferred general method of the invention can be described, for example, with reference to FIG. 1, in which particles 10 bounded by a barrier 15 such as a vessel are fluidized to form a multi-phase system 12 comprising the fluidized particles 10 and a gaseous continuous phase. Such particles can be, for example, reaction products such as polymer particles, reaction adjuncts such as catalysts, etc., and other solid particles. One or more mechanical resonators (designated generally collectively using the reference numeral "40," with multiple resonators designated more specifically in the various figures as resonators with circled numbers 1, 2, 3, etc. and in the associated text herein as 40-1, 40-2, 40-3, etc.) are placed in contact with the fluidized particles. The mechanical resonator is stimulated to generate a response of the mechanical resonator. The stimulation can be caused by impact of the fluidized particles against the mechanical resonator, or by application of an external stimulus such as an electrical current or physical stimulation, or by both. The response of the mechanical resonator is monitored by processing unit 50, and the multi-phase system is characterized. In preferred embodiments, for example, the multi-phase system can be characterized by determining some measurable parameter such as (i) a localized density, (ii) a granular temperature, (iii) a mixing factor, and/or (iv) an elastic modulus based on the monitored response of the mechanical resonator.

In another preferred general approach of the general method, the mechanical resonator sensor 40 is placed in contact with a multi-phase system 12 comprising non-fluidized (e.g., static) particles and a gaseous continuous phase. The mechanical resonator is stimulated by some mechanism other than impact of particles thereagainst, e.g., an electrical current or physical stimulation. Again, the response of the mechanical resonator is monitored by processing unit 50, and the multi-phase system is characterized. For example, the multi-phase system can be characterized by determining some measurable parameter such as (i) a localized density, (ii) a granular temperature, (iii) a mixing factor, and/or (iv) an elastic modulus based on the monitored response of the mechanical resonator.

Figure 2:
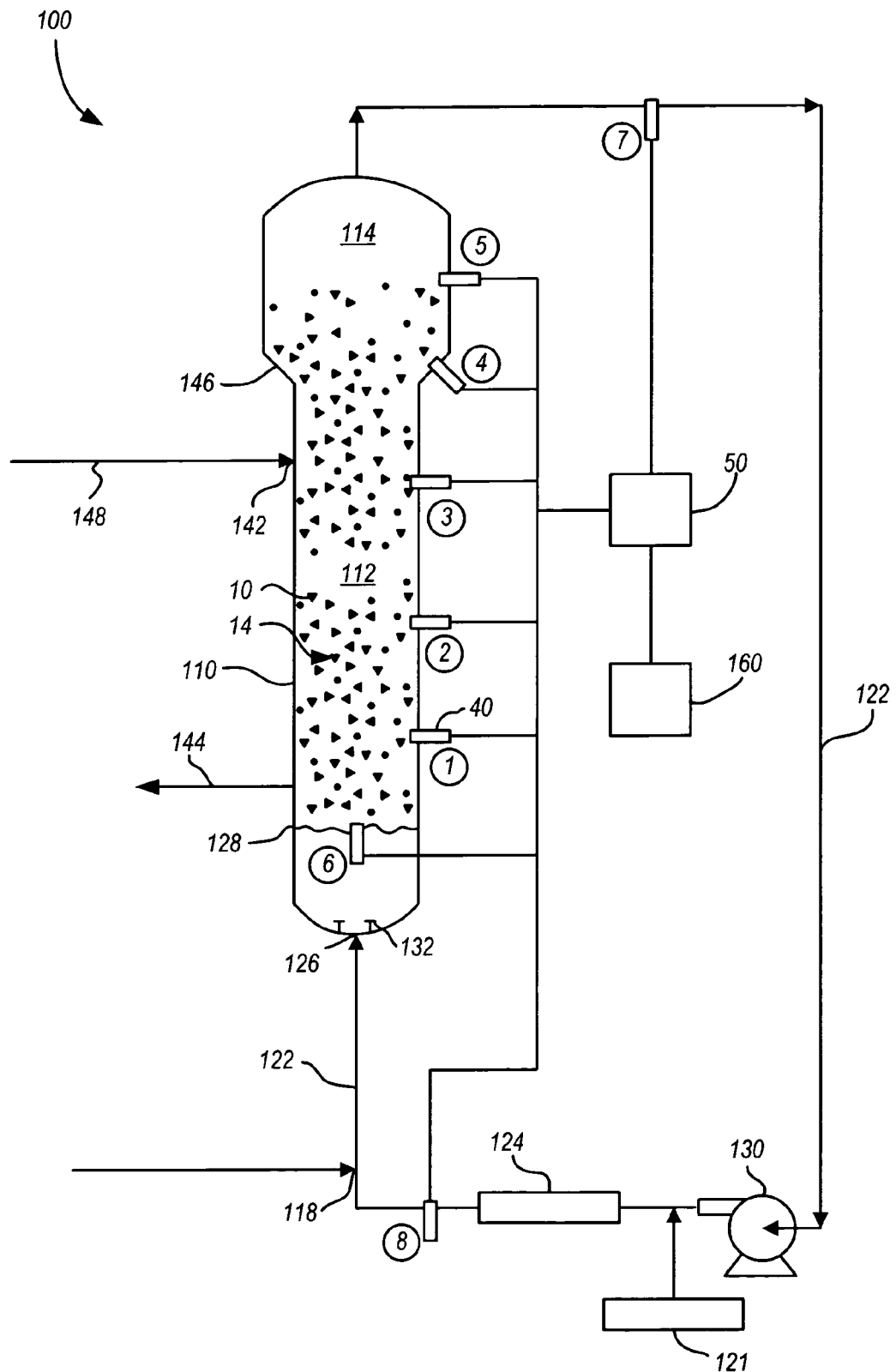
FIG. 2 is a schematic representation of the general methods, systems and/or apparatus of the-invention illustrating implementation in a fluidized bed polymerization reactor.

In a further generally preferred approach of the general method, with reference to FIG. 2, polymer particles 10 in a fluidized bed polymerization reactor system 100 are monitored for purposes of characterizing the particles, or characterizing the multi-phase system forming the fluidized bed 14, as described above, as well as for monitoring the polymerization reaction, process control, etc. According to the general method, a gaseous monomer is added to the fluidized bed polymerization reactor 110 of the reactor system 100 thereby forming fluidized polymer particles 10 in a gas phase polymerization reaction in the fluidized bed polymerization reactor vessel 110. A mechanical resonator 40-1 is contacted with the fluidized polymer particles in the reactor system. A response of the mechanical resonator is monitored. Based on a monitored response of the mechanical resonator, one or more events or parameters can be determined, as illustrated by the following nonexclusive list: (i) an occurrence or extent of agglomeration of the fluidized polymer particles in the reactor system, (ii) an occurrence or extent of polymer sheeting in the reactor system, (iii) a rate of polymerization in the fluidized bed polymerization reactor, (iv) a level of condensed liquid in the fluidized bed polymerization reactor, (v) an occurrence or extent of channeling of the fluidized polymer particles in the reactor system, (vi) an occurrence or extent of fluidization of the polymer particles in the reactor system, (vii) an occurrence or extent of plugging of a gas distribution plate 128 in the reactor system, and (viii) the occurrence or extent of scrubbing of the transition cone in the fluidized bed polymerization reactor. The response of the mechanical resonator can also be used to vary a process condition of the reactor system by coupling a process controller 160 to the processing unit 50. The process controller 160 is in turn coupled to the compressor 130, hear exchanger 124, valves, etc. Mechanical resonators 40 can be placed in many different positions in the reactor system 100 besides the reactor vessel 110, as illustrated by mechanical resonators 40-1, 40-2, 40-3, 40-4, 40-5, 40-6, 40-7, 40-8. Further details of fluidized bed polymerization reactor systems and mechanical resonators including specific apparatus adapted for such monitoring are described below, and each of the below-described details are specifically considered in various combination with these and other generally preferred approaches described herein.

Each of the aforementioned generally preferred approaches can be applied independently or in combination with each other, in each of the possible various permutations. Also, each of the aforementioned generally preferred approaches can be applied in further combination with more particular aspects, including particular protocols and/or particular apparatus features, as described below.

Preferred General Systems Apparatus

The present invention also includes devices effective for monitoring particles and multi-phase systems in fluidized beds according to the aforementioned methods. In general, such devices are systems or apparatus that comprise one or more mechanical resonator sensors, including mechanical resonator sensors adapted to form an interfaced sensor that is operational or that has enhanced operational functionality.

A preferred general system of the invention can comprise a mechanical resonator sensor 40 adapted to interface a barrier 15 (e.g., vessel or reactor 110), where the interfaced sensor comprises a sensing element, and is in communication with at least one or both of a data retrieval circuit or a signal processing circuit of the processing unit 50 that receives output from the mechanical resonator.

Figure 3:
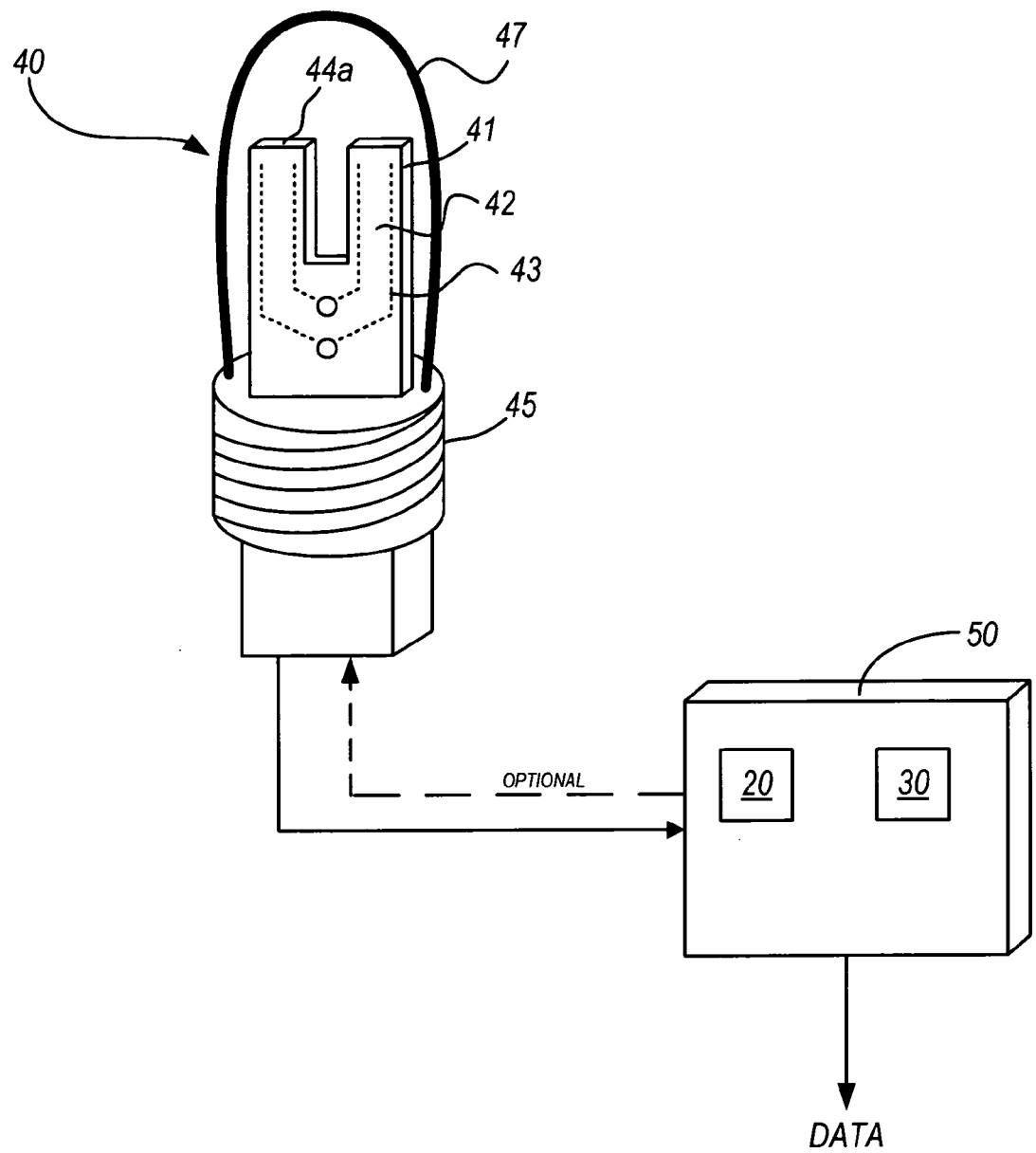
FIG. 3 is a perspective view of a preferred apparatus of the invention

In this respect, with reference to FIG. 3, in one preferred general embodiment the sensor 40 includes a mechanical resonator 41 having a sensing surface 42 adapted for exposure to a multi-phase system comprising fluidized or nonfluidized particles in at least one of a gaseous continuous phase and a liquid phase. A signal processing circuit 20 or data retrieval circuit 30 of the processing unit 50 is in electrical communication with the flexural resonator for receiving an output signal from the flexural resonator during a sensing period. The signal processing circuit is configured for processing the received signal to generate data representing, for example, a localized density of the fluidized particles, a granular temperature of the fluidized particles, a mixing factor of the fluidized particles and combinations thereof. Further details of this preferred general embodiment, including preferred structural elements and uses thereof are described herein (above and below), and each of the herein-described details are specifically considered in combination with this and other generally described features of the systems and apparatus.

In another preferred general embodiment, with reference again to FIGS. 2 and 3, a fluidized bed polymerization reactor system 100 includes a reaction vessel 110 (also referred to interchangeably herewith as a reactor vessel) having an inlet port 126, the inlet port being adapted for receiving a gaseous fluid for fluidizing polymer particles in the reaction vessel. A mechanical resonator sensor 40 includes a sensing surface 42 adapted for exposure to the fluidized polymer particles within the reactor system.

The invention is also directed to various apparatus for use (alone or as part of a monitoring system) in monitoring one or more properties of particles in fluidized beds and fluidized bed polymerization reactor system using one or more flexural resonators.

Each of the aforementioned generally preferred systems or apparatus can be applied independently or in combination with each other, in each of the possible various permutations. Also, each of the aforementioned generally preferred approaches can be applied in further combination with more particular aspects, including particular methodology protocols and/or particular apparatus features, as described above and/or below.

Monitoring of Fluidized Beds and Multi-Phase Systems— General Considerations

In each of the aforementioned generally preferred approaches and/or embodiments, the sensor(s) can be employed for monitoring and/or characterizing one or more types of particles and multi-phase systems in both fluidized bed systems and non-fluidized bed systems.

Fluidized Bed Systems (Including Fluidized Bed Polymerization Reactor Systems)

A fluidized bed can generally include a bed particles in which the static friction between the particles is disrupted. In each of the aforementioned generally preferred approaches and/or embodiments, the fluidized bed system can be an open fluidized bed system or a closed fluidized bed system. An open fluidized bed system can comprise one or more fluids and one or more types of fluidized solid particles and having one or more fluidized bed surfaces that are exposed to an open uncontrolled atmosphere. For example, an open fluidized bed system can be an open container such as an open-top tank or an open well of a batch reactor or of a parallel batch reactor (e.g., microtiter chamber). Alternatively, the fluidized bed system can be a closed fluidized bed system. A closed fluidized bed system can comprise one or more fluids and one or more types of fluidized particles that are generally bounded by a barrier so that the fluids and particles are constrained. For example, a closed fluidized bed system can include a pipeline (e.g., for particle transport); a recirculating fluidized bed system, such as the fluidized bed polymerization reactor system of FIG. 2 (discussed above and below); or a solids drying system; any of which may be associated with various residential, commercial and/or industrial applications.

A closed fluidized bed system can be in fluid communication with an open fluidized bed system. The fluid communication between a closed fluidized bed system and an open fluidized bed system can be isolatable, for example, using one or more valves. Such isolation valves can be configured for unidirectional fluid flow, such as for example, a pressure relief valve or a check valve. In general, the fluidized bed system (whether open or closed) can be defined by manufactured (e.g., man-made) boundaries comprising one or more barriers. The one or more barriers defining manufactured boundaries can generally be made from natural or non-natural materials. Also, in general, the fluidized bed system (whether open or closed) can be a flow system such as a continuous flow system or a semi-continuous flow (e.g., intermittent-flow) system, a batch system, or a semi-batch system (sometimes also referred to as a semi-continuous system). In many instances, fluidized bed systems that are flow systems are closed fluidized bed systems.

The fluidized bed in preferred embodiments is generally formed by flow of a gaseous fluid in a direction opposite gravity. The frictional drag of the gas on the solid particles overcomes the force of gravity and suspends the particles in a fluidized state referred to as a fluidized bed. To maintain a viable fluidized bed, the superficial gas velocity through the bed must exceed the minimum flow required for fluidization. Increasing the flow of the fluidizing gas increases the amount of movement of the particles in the bed, and can result in a beneficial or detrimental tumultuous mixing of the particles. Decreasing the flow results in less drag on the particles, ultimately leading to collapse of the bed. Fluidized beds formed by gases flowing in directions other than vertically include particles flowing horizontally through a pipe, particles flowing downwardly e.g., through a downcomer, etc.

Fluidized beds can also be formed by vibrating or otherwise agitating the particles. The vibration or agitation keeps the particles in a fluidized state.

Fluidized Bed Polymerization Reactor Systems

In each of the aforementioned generally preferred approaches and/or embodiments, the fluidized bed system can include a fluidized bed polymerization reactor system. As briefly noted above, gas phase polymerization reactions may be carried out in fluidized bed polymerization reactors, and can also be formed in stirred or paddle-type reaction systems (e.g., stirred bed systems) which include solids in a gaseous environment. While the following discussion will feature fluidized bed systems, where the present invention has been found to be preferred and especially advantageous, it is to be understood that the general concepts relating to the use of the mechanical resonator sensors, which are discussed relevant to the preferred fluidized bed systems, are also adaptable to the stirred or paddle-type reaction systems as well. The present invention is not limited to any specific type of gas phase reaction system.

In very general terms, a conventional fluidized bed polymerization process for producing resins and other types of polymers is conducted by passing a gaseous stream containing one or more monomers continuously through a fluidized bed reactor under reactive conditions and in the presence of catalyst at a velocity sufficient to maintain the bed of solid particles in a suspended condition. A continuous cycle is employed where the cycling gas stream, otherwise known as a recycle stream or fluidizing medium, is heated in the reactor by the heat of polymerization. The hot gaseous stream, also containing unreacted gaseous monomer, is continuously withdrawn from the reactor, compressed, cooled and recycled into the reactor. Product is withdrawn from the reactor and make-up monomer is added to the system, e.g., into the recycle stream or reactor vessel, to replace the polymerized monomer. See for example U.S. Pat. Nos. 4,543,399, 4,588, 790, 5,028,670, 5,317,036, 5,352,749, 5,405,922, 5,436,304, 5,453,471, 5,462,999, 5,616,661, 5,668,228, and 6,689,847 all of which are fully incorporated herein by reference. A basic, conventional fluidized bed system is illustrated in FIG. 2. The reactor 110 comprises a reaction zone 112 and a velocity reduction zone 114. While a reactor configuration comprising a generally cylindrical region beneath an expanded section is shown in FIG. 2, alternative configurations such as a reactor configuration comprising an entirely or partially tapered reactor may also be utilized. In such configurations, the fluidized bed can be located within a tapered reaction zone but below a region of greater cross-sectional area which serves as the velocity reduction zone of the more conventional reactor configuration shown in FIG. 2.

In general, the height to diameter ratio of the reaction zone can vary in the range of about 2.7:1 to about 5:1. The range may vary to larger or smaller ratios and depends mainly upon the desired production capacity. The cross-sectional area of the velocity reduction zone 114 is typically within the range of from about 2.5 to about 2.9 multiplied by the cross-sectional area of the reaction zone 112.

The reaction zone 112 includes a bed of growing polymer particles, formed polymer particles and a minor amount of catalyst all fluidized by the continuous flow of polymerizable and modifying gaseous components, including inerts, in the form of make-up feed and recycle fluid through the reaction zone. To maintain a viable fluidized bed, the superficial gas velocity through the bed must exceed the minimum flow required for fluidization which is typically from about 0.2 to about 0.5 ft/sec. for polyolefins. Preferably, the superficial gas velocity is at least 0.2 ft/sec above the minimum flow for fluidization or from about 0.4 to about 0.7 ft/sec. Ordinarily, the superficial gas velocity will not exceed 5.0 ft/sec and is usually no more than about 2.5 ft/sec.

On start-up, the reactor is generally charged with a bed of particulate polymer particles before gas flow is initiated. Such particles help to prevent the formation of localized "hot spots" when catalyst feed is initiated. They may be the same as the polymer to be formed or different. When different, they are preferably withdrawn with the desired newly formed polymer particles as the first product. Eventually, a fluidized bed consisting of desired polymer particles supplants the start-up bed.

Fluidization is achieved by a high rate of fluid recycle to and through the bed, typically on the order of about 50 times the rate of feed or make-up fluid. This high rate of recycle provides the requisite superficial gas velocity necessary to maintain the fluidized bed. The fluidized bed has the general appearance of dense mass of individually moving particles as created by the percolation of gas through the bed. The pressure drop through the bed is equal to or slightly greater than the weight of the bed divided by the cross-sectional area.

Referring again to FIG. 2, make-up fluids can be fed at point 118 via recycle line 122. The composition of the recycle stream is typically measured by a gas analyzer 121 and the composition and amount of the make-up stream is then adjusted accordingly to maintain an essentially steady state gaseous composition within the reaction zone. The gas analyzer 121 can be positioned to receive gas from a point between the velocity reduction zone 114 and heat exchanger 124, preferably, between compressor 130 and heat exchanger 124.

To ensure complete fluidization, the recycle stream and, where desired, at least part of the make-up stream can be returned through recycle line 122 to the reactor, for example at point 126 below the bed. Preferably, there is a gas distributor plate 128 above the point of return to aid in fluidizing the bed uniformly and to support the solid particles prior to start-up or when the system is shut down. The stream passing upwardly through and out of the bed helps remove the heat of reaction generated by the exothermic polymerization reaction.

The portion of the gaseous stream flowing through the fluidized bed which did not react in the bed becomes the recycle stream which leaves the reaction zone 112 and passes into the velocity reduction zone 114 above the bed where a major portion of the entrained particles drop back onto the bed thereby reducing solid particle carryover.

The recycle stream is then compressed in compressor 130 and passed through heat exchanger 124 where the heat of reaction is removed from the recycle stream before it is returned to the bed. Note that the heat exchanger 124 can also be positioned before the compressor 130. The recycle stream exiting the heat exchange zone is then returned to the reactor at its base 126 and thence to the fluidized bed through gas distributor plate 128. A fluid flow deflector 132 is preferably installed at the inlet to the reactor to prevent contained polymer particles from settling out and agglomerating into a solid mass and to maintain entrained or to re-entrain any particles or liquid which may settle out or become disentrained.

Particulate polymer product is discharged from line 144. Although not shown, it is desirable to separate any fluid from the product and to return the fluid to the reactor vessel 110.

In accordance with an embodiment of the present invention, the polymerization catalyst enters the reactor in solid or liquid form at a point 142 through line 148. If the catalyst requires the use of one or more co-catalysts, as is usually the case, the one or more cocatalysts may be introduced separately into the reaction zone where they will react with the catalyst to form the catalytically active reaction product. However the catalyst and cocatalyst(s) may be mixed prior to their introduction into the reaction zone.

The reactor shown in FIG. 2 is particularly useful for forming polyolefins such as polyethylene, polypropylene, etc. Process conditions, raw materials, catalysts, etc. for forming various polyolefins and other reaction products are found in the references incorporated herein. Illustrative process conditions for polymerization reactions in general are listed below to provide general guidance.

The reactor pressure in a gas phase process may vary from about 100 psig (690 kPa) to about 600 psig (4138 kPa), preferably in the range of from about 200 psig (1379 kPa) to about 400 psig (2759 kPa), more preferably in the range of from about 250 psig (1724 kPa) to about 350 psig (2414 kPa).

The reactor temperature in a gas phase process may vary from about 30° C. to about 120° C., preferably from about 60° C. to about 115° C., more preferably in the range of from about 70° C. to about 110° C., and most preferably in the range of from about 70° C. to about 95° C.

Other gas phase processes contemplated include series or multistage polymerization processes. Also gas phase processes contemplated by the invention include those described in U.S. Pat. Nos. 5,627,242, 5,665,818 and 5,677,375, and European publications EP-A-0 794 200, EP-B1-0 649 992, EP-A-0 802 202, and EP-B-634 421 all of which are herein fully incorporated by reference.

In a preferred embodiment, the reactor utilized in the present invention is capable of producing greater than 500 lbs of polymer per hour (227 Kg/hr) to about 200,000 lbs/hr (90,900 Kg/hr) or higher of polymer, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and most preferably greater than 65,000 lbs/hr (29,000 Kg/hr) to greater than 100,000 lbs/hr (45,500 Kg/hr).

Figure 4:
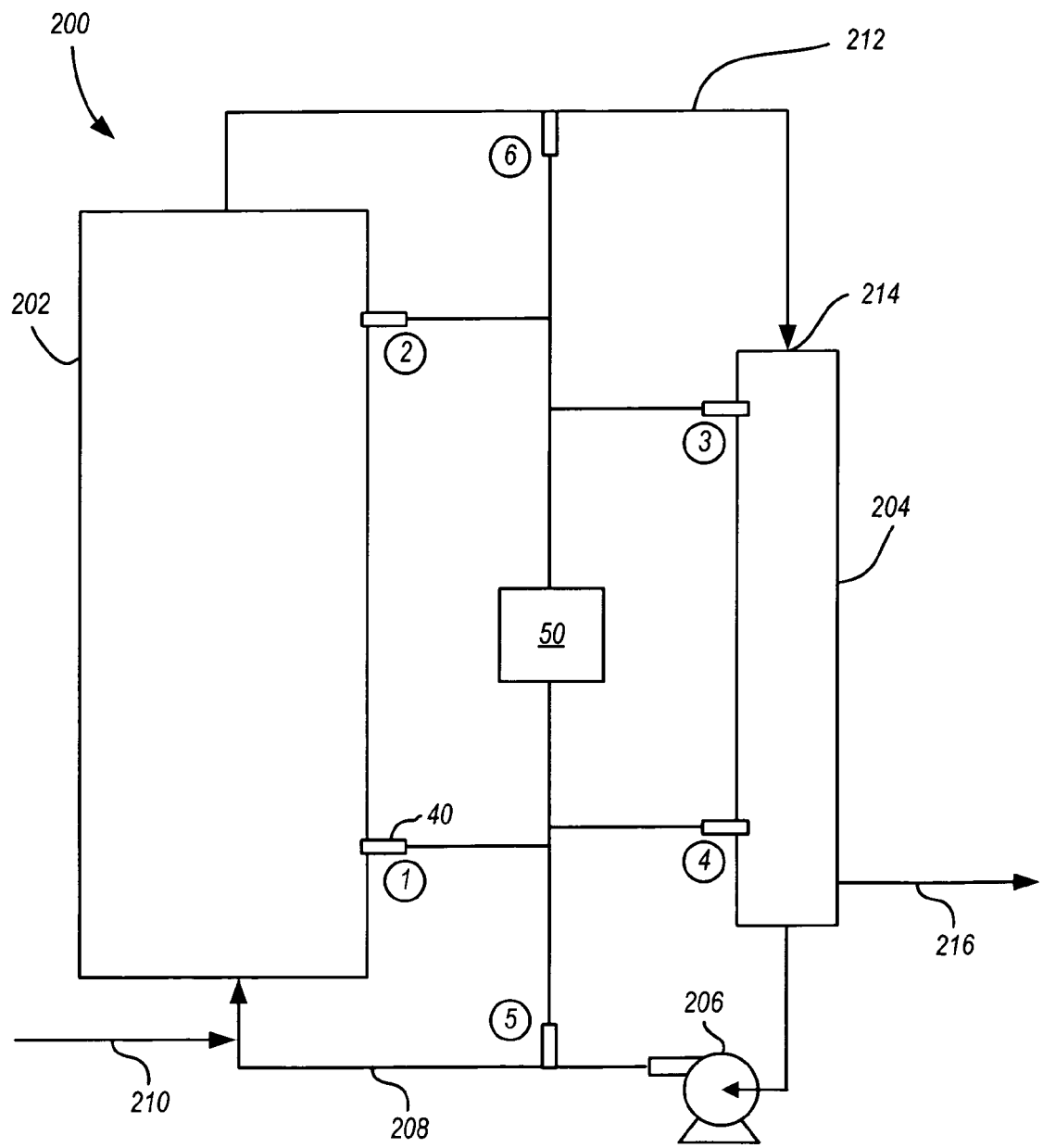
FIG. 4 is a schematic representation of the general methods, systems and/or apparatus of the invention illustrating implementation in a fluidized bed polymerization reactor.

Another illustrative fluidized bed polymerization reactor system 200 is shown in FIG. 4. As shown, the system 200 is a recirculating system including a fast riser 202, a downcomer 204, and a recirculating pump 206. The monomer(s) and catalyst are added to recycle line 208 via feed 210. In this type of system, the polymerization product is formed primarily in the fast riser, but continues to form throughout the system. Polymer particles formed in the fast riser 202 pass through line 212 to an upper inlet port 214 of the downcomer 204. The polymer particles gather in the downcomer, where they move downwardly in a dense, slow moving bed. The bed formed in the downcomer can be considered a fluidized bed. Particulate polymer product is discharged from line 216. Although not shown, it is desirable to separate any fluid from the product and to return the fluid to the reactor vessel 110.

Other Types of Bed Systems

Slower moving masses of particles, while considered "fluidized" for purposes of the invention, are also referred to in the art as "moving beds." Moving beds include particles in such things as mass flow bins, downcomers, etc. where solids are slowly moving through a vessel.

Stirred bed system, while considered "fluidized" for purposes of the invention, include beds stirred or otherwise agitated by a member such as a paddle or plunger rotating or moving through the bed (e.g., stirred bed reactor, blender, etc.). Other types of stirred bed systems can be formed by a rotating drum (e.g., with or without internal baffles to enhance mixing), a vessel moving in a see-saw manner, agitation including ultrasonic vibrations applied to the particles or their container, etc.

Nonfluidized Bed Systems

In each of the aforementioned generally preferred approaches and/or embodiments, the non-fluidized system can be similar to the fluidized systems described above in terms of structure and composition, except that the particles are not fluidized. Rather the particles are at rest with a gaseous fluid in interstitial spaces defined between the polymer particles. For instance, the non-fluidized system can be an open system or a closed system. Additionally, the non-fluidized system can merely be a fluidized system at rest. One or more mechanical resonators 40 can be positioned at various locations in the nonfluidized bed such that the mechanical resonators 40 contact the particles. Illustrative locations include along the wall of a vessel containing the particles, along the top or bottom of the bed, in the middle of the bed, and/or at some point therebetween.

Fluids

In general, for example, mechanical resonators such as flexural resonators can be used in connection with liquids or fluidizing gasses having a wide range of fluid properties, such as a wide range of viscosities, densities and/or dielectric constants (each such property being considered independently or collectively as to two or more thereof). For example, liquid fluids can generally have viscosities ranging from about 0.1 cP to about 100,000 cP, and/or can have densities ranging from about 0.0005 g/cc^3 to about 20 g/cc^3 and/or can have a dielectric constant ranging from about 1 to about 100. In many embodiments of the invention, the fluidizing continuous phase media is a gaseous fluid. Gaseous fluids can, for example, generally have viscosities ranging from about 0.001 to about 0.1 cP, and/or can have densities ranging from about 0.0005 to about 0.1 g/cc^3 and/or can have a dielectric constant ranging from about 1 to about 1.1.

The fluidizing gasses and raw materials of the invention can include relatively pure gaseous elements (e.g., gaseous $N_2$, gaseous $O_2$). Other components can include relatively pure liquid, solid, or gaseous compounds (e.g., liquid or solid catalyst, gaseous monomer $CH_2$=$CH_2$ or $CH_2$=Cl, air). The various fluidized and non-fluidized beds of the inventions can also include single-phase or multi-phase mixtures of gases, solids and/or liquids, including for example: two-phase mixtures of solids and gases (e.g., fluidized bed systems), mixtures of gasses with a single type of particle, mixtures of gasses with different types of particles (e.g., polymer and catalyst particles); and/or three-phase mixtures of gasses, liquids and solids (e.g., fluidized bed with liquid catalyst being added). Particular examples of preferred fluids are described herein, including in discussion below regarding preferred applications of the methods and devices of the invention.

Particles

The particles sought to be monitored by the present invention include any type of solid or semi-solid particle, such as polymer particles, catalyst particles, etc. The size, shape, mass, composition, hardness, etc. of the particles is not critical to the invention.

Operating Conditions

The operating conditions of the fluidized and nonfluidized bed systems is not narrowly critical to the invention. While general operating conditions have been provided above for fluidized bed polymerization reactor systems, fluidized and nonfluidized bed systems can, in addition to those listed above, have widely varying process conditions, such as temperature, pressure, fluidizing gas flowrate, etc. Generally, the temperature will be above the vaporization temperature of the fluidizing fluid, including for example to superheated temperatures. Particular temperature ranges can be preferred for particular fluids. Generally, the pressure within a fluidized or nonfluidized bed system can likewise cover a wide range, including for example ranging from about vacuum conditions to about 25,000 psig. In preferred applications, the pressure can be lower, ranging from vacuum conditions to about 15,000 psig, from vacuum conditions to about 10,000 psig, from vacuum conditions to about 5,000 psig, from vacuum conditions to about 1,000 psig, from vacuum conditions to about 500 psig, or from vacuum conditions to about 100 psig. In an alternative embodiment, the pressure range in each of the aforementioned ranges can have lower pressure limit of about 1 psig or about 10 psig or about 20 psig.

Sensors

In general, as noted above, the particular mechanical resonator sensor of the methods and systems and apparatus of the present invention is not limited. Generally, the sensors useful in connection with this invention are adapted to monitor one or more properties of a fluidized or nonfluidized bed of particles and/or a multi-phase system comprising the particles and a gaseous continuous phase. By "monitoring" what is meant is to generate data associated with one or more properties of the particles or multi-phase system. The data association with a property in this context means data (typically obtained or collected as a data stream over some time period such as a sensing period), including both raw data (directly sensed data) or processed data, can be directly informative of or related to (e.g., through correlation and/or calibration) an absolute value of a property and/or a relative value of a property (e.g., a change in a property value over time), and can be used to characterize the particles and/or multi-phase system. In many applications, the raw data can be associated with a property of interest using one or more correlations and/or using one or more calibrations. Typically such correlations and/or calibrations can be effected electronically using signal processing circuitry, either with user interaction or without user interaction (e.g., automatically).

Particular mechanical resonator sensors can be selected based on needed or desired property (or properties) of interest, and on required specifications as to sensitivity, universality, fluid-compatibility, system-compatibility, as well as on business considerations such as availability, expense, etc.

The mechanical resonator can include, for example, flexural resonators, surface acoustic wave resonators, thickness shear mode resonators and the like. Various types of flexural resonators can be employed, including for example tuning forks, cantilevers, bimorphs, unimorphs, membrane resonators, disc benders, torsion resonators, or combinations thereof. Flexural resonator sensing elements comprising tuning fork resonators are particularly preferred. The tuning fork resonator can have two tines (e.g., binary-tined tuning fork) or more than two tines, such as three tines (e.g., a trident tuning fork) or four tines (e.g., a quaternary-tined tuning fork). The tuning fork resonator can also include multiple sets of tines (e.g., two tuning forks coupled to the same mount). In some applications, a tuning fork resonator may be configured (e.g., with respect to geometry and electrode configuration) for resonating within a single plane. For some applications, a tuning fork may be may be configured (e.g., with respect to geometry and electrode configuration) for resonating in two or more different planes relative to each other, such as in two planes perpendicular to each other.

A tuning fork-type sensor 40 in one approach is comprised of a piezoelectric crystal, e.g., of $LiNbO_3$, that is cut into the shape of a tuning fork, as is shown schematically in FIG. 3. Electrodes 43 are embedded between covalently bonded crystal layers. Due to the piezoelectric effect, the mechanical resonator sensor 40 generates an electrical signal in response to oscillations of the tines of the fork, which can be induced from impacts by particles, for example. Thus the fork can be used to "listen" for particle impacts in a passive sense. Likewise, if an oscillating voltage is applied across the electrodes, the fork will be driven into oscillations, with displacement in the tines on the order of, for example, 100 nm. In this mode, the fork actively interacts with its surroundings. Moreover, the sensor 40 can still "listen" for impacts while it is in active mode operation since the effects are additive over the small displacements realized in the crystal.

Such flexural resonator sensors are well known in the art. See Matsiev, "*Application of Flexural Mechanical Resonators to Simultaneous Measurements of Liquid Density and Viscosity*," IEEE International Ultrasonics Symposium, Oct. 17-20, 1999, Lake Tahoe, Nev., which is incorporated by reference herein for all purposes, and see also U.S. Pat. Nos. 6,401,519; 6,393,895; 6,336,353; 6,182,499; 6,494,079 and EP 0943091 B1, each of which are incorporated by reference herein for all purposes. More recent advances include those described in co-pending applications, such as U.S. Ser. No. 10/452,264 entitled "Machine Fluid Sensor And Method" filed on Jun. 2, 2003 by Matsiev et al. and now U.S. Pat. No. 7,043,969 (describing applications involving flexural resonator technologies in machines, such as transportation vehicles); U.S. Ser. No. 60/505,943 entitled "Environmental Control System Fluid Sensing System and Method" filed on Sep. 25, 2003 by Matsiev et al. and related PCT Application No. PCT/US03/32983 entitled "Environmental Control System Fluid Sensing System and Method" filed on Oct. 17, 2003 by Matsiev et al. (describing applications involving flexural resonator technologies in heating, ventilation, air-conditioning and refrigeration systems and in machines such as engine systems related thereto); US Appl. No. 2002/0178805 A1 (describing applications involving flexural resonator technologies in down-hole oil well applications such as well-logging systems); U.S. Ser. No. 10/804,446 entitled "Mechanical Resonator" filed on Mar. 19, 2004 by Kolosov et al. and now U.S. Pat. No. 7,210,332 (describing various advantageous materials and coatings for flexural resonator sensing elements); U.S. Ser. No. 10/804,379 entitled "Resonator Sensor Assembly" filed on Mar. 19, 2004 by Kolosov et al., and published as U.S. Appl. No. 2004/0250622 (now abandoned), and PCT Application. No. PCT/US04/08552 entitled "Resonator Sensor Assembly" filed on Mar. 19, 2004 by Kolosov et al. (describing various advantageous packaging approaches for applying flexural resonator technologies); and U.S. Ser. No. 10/394,543 entitled "Application Specific Integrated Circuitry For Controlling Analysis For a Fluid" filed on Mar. 21, 2003 by Kolosov et al., and PCT Application. No. PCT/US2004/008555 entitled "Application Specific Integrated Circuitry For Controlling Analysis a Fluid" filed on Mar. 19, 2004 by Kolosov et al. (describing electronics technologies involving application-specific integrated circuit for operating flexural resonator sensing elements), each of which are incorporated herein by reference for all purposes, and each of which includes descriptions of preferred embodiments for flexural resonator sensors and use thereof in connection with the methods and apparatus and systems of the present invention. Further details regarding flexural resonator sensors and/or flexural resonator sensing elements are described below, but are generally applicable to each approach and/or embodiment of the inventions disclosed herein.

In one approach, with reference to FIG. 3, a protective member 47 may be added to the sensor assembly to protect the mechanical resonator from damage due to impact with very large agglomerated particles and/or falling sheets. In a commercial-scale facility, a cage may be used as a protective member 47 for the sensor assembly. The size and distribution of the openings in the cage can be selected to allow small particles to pass through the cage while preventing large agglomerated particles from contacting the sensor. It may also be beneficial if the exposed portion of the mechanical resonator itself were also shorter than about 1 inch, since this would allow for a shorter, stiffer cage. Along with the cage, very strong (e.g. ⅜" O.D.) external protection pins could be provided along side the cage to deflect impacts from large agglomerates in the bed.

Although much of the description is presented herein in the context of flexural resonator sensors, various aspects of the invention are not limited to such sensors.

Hence, other types of sensors (or sensor subassemblies) can also be used in place of mechanical resonators.

In addition, other types of sensors (or sensor subassemblies) can be used in combination with the mechanical resonator sensor or other types of sensors mentioned above. Particularly preferred sensors for use in combination with mechanical resonators, such as flexural resonators, include temperature sensors, pressure sensors, flow sensors, conductivity sensors, thermal conductivity sensors, among others.

With further reference to FIG. 1, in one approach, the sensor 40 can comprise one or more sensing elements 44*a*, 44*b* (e.g., a flexural resonator and a temperature sensing element as in sensor 40-1, in combination, or alternatively, e.g., two or more mechanical resonators such as two or more flexural resonators as in sensor 40-2), optionally coupled to a sensor housing 45 such that a sensing surface of the sensing elements 44*a*, 44*b* can be exposed to the particles (e.g., via vessel port 16). The sensor housing 45 may further include a threaded portion (shown in FIG. 3) for engaging a complimentary threaded port 16 of the barrier 15. A ported and installed sensor 40 can also optionally comprise a detachable coupling 60 providing electrical or mechanical access across the barrier.

While the sensor 40 is described above and below in terms of being coupled to an external processing unit 50 having a signal processing circuit 20 and data retrieval circuit 30, the circuitry may also be implemented with the sensor in a single standalone unit. As one preferred example, the sensor 40 can comprise a sensing element (e.g., a flexural resonator), a signal processing circuit 20 (e.g., comprising amplifier circuitry), and a data retrieval circuit 30 (e.g. comprising data memory circuitry, perhaps adapted for recording raw data received from the sensing element). More specifically, in a preferred embodiment the fluidized or nonfluidized system can comprise one or more installed sensing elements 44*a*, 44*b* (e.g., two or more flexural resonator sensing elements), and both an installed signal processing circuit 20, and an installed data retrieval circuitry 30. The particular location of the signal processing circuitry 20 and/or data retrieval circuitry 30 of the installed sensor 40 is not critical. In some embodiments (e.g., in applications involving high-temperature and/or flammable fluids), it may be advantageous to provide the preinstalled circuitry 20, 30 external to the barrier 15 (e.g., fixedly mounted on a surface of the barrier 15 opposing the fluid-side surface of the barrier 15), and in electrical communication with one or more of the sensors 44*a*, 44*b*. In other embodiments the circuitry 20, 30 can be mounted on the fluid-side surface of the barrier 15. In any case, in operation, collected data residing in an installed memory circuit of the sensor can be transmitted to and either displayed in or stored in a ported unit, for later collection and/or analysis at a remote data repository. For example, the ported unit could include a port for portable memory such as a memory stick (jump drive), allowing the data to be transferred to a remote data repository via such memory stick (jump drive).

Sensor Positioning

With further reference to FIGS. 1, 2 and 4, in an embodiment, the mechanical resonator sensors 40 can be placed in many different positions along or in the system containing the fluidized or nonfluidized bed of particles.

For instance, in the fluidized bed polymerization reactor system 100 of FIG. 2, some sensors, e.g., 40-1, 40-2, 40-3, 40-4, 40-5, 40-6 have sensing surfaces positioned in the reactor vessel 110. Other sensors e.g., 40-7, 40-8, can be positioned at virtually any position along the recirculation system. Sensors 40-1, 40-2, 40-3 are ported sensors that pass through the reactor vessel 110 such that the sensing surface of each sensor 40 is exposed to the fluidized particles in the reaction zone 112. Sensor 40-6 is mounted to the gas distribution plate 128, and its response can indicate an occurrence or extent of plugging of the gas distribution plate. The sensing surface of sensors 40-1, 40-2, 40-3, 40-6 are impacted by the fluidized particles. The responses of the sensors here can be used to monitor and characterize such things as variations in reaction rate, localized density, granular temperature, mixing factor, elastic modulus, level sensing, etc. in the reaction zone 112. Several of these properties and characteristics are described above and below.

With continued reference to FIG. 2, sensor 40-5 is a ported sensor having a sensing surface exposed to the fluidized particles in the velocity reduction zone 114. The responses of the sensor here can be used to monitor and characterize such things as reaction zone overflow, localized density, granular temperature, etc. in the velocity reduction zone 114. Several of these properties and characteristics are described above and below.

Use of a sensor 40-4 just above the reaction zone 112 in the transition cone 146 to the velocity reduction zone 114 is also beneficial. For many systems, keeping the fluidized bed at an appropriate level so that bursting bubbles scrub this transition cone 146 helps to prevent sheeting there. The mechanical resonator 40-4 is a direct way to measure the effectiveness of scrubbing in the transition cone 146, rather than inferring this from bed level measurements Mechanical resonator sensors 40-7, 40-8 are positioned in the recycle system and can be used to monitor such things as localized density, granular temperature, etc. of particles passing through the recycle system. While the sensors are shown as on the recycle line 122, sensors can also be positioned in the various components such as in the heat exchanger 124.

With reference to FIG. 4, sensors 40-1, 40-2, 40-3, 40-4, 40-5, 40-6 are positioned in the fast riser 202, downcomer 204 and recirculation lines 208, 212.

Ported sensors are preferred because they are easy to remove and clean should fouling occur. Ported sensors are also easier to replace should some event such as sheeting destroy or otherwise render the sensor inoperable.

Sensor Circuitry

In preferred embodiments, one or more circuit modules of the signal processing circuit and/or the data retrieval circuit can be implemented and realized as an application specific integrated circuit (ASIC). See, for example, above-referenced U.S. Ser. No. 10/394,543 entitled "Application Specific Integrated Circuitry For Controlling Analysis For a Fluid" filed on Mar. 21, 2003 by Kolosov et al., and PCT Application. No. PCT/US2004/008555 entitled "Application Specific Integrated Circuitry For Controlling Analysis For a Fluid" filed on Mar. 19, 2004 by Kolosov et al. Particularly preferred circuit configurations are described below, but should be considered generally applicable to each approach and embodiment of the inventions described herein.

Barrier Interface

As described above in connection with the generally preferred approaches, systems, and apparatus (e.g., in connection with FIGS. 1 and 3), a ported sensor or ported sensor subassembly can be interfaced with the fluidized or nonfluidized system across a barrier 15 that defines at least a portion of the fluidized or nonfluidized system. Preferably, the ported sensor, the sensor or sensor subassembly is interfaced across the barrier without substantially compromising the integrity of the fluidized or nonfluidized system.

With further reference to FIGS. 1 and 3, a ported sensor subassembly can be interfaced with a fluidized or nonfluidized system across a barrier 15 via a coupling such as a portion of the sensor housing 45. The coupling can generally be a mechanical coupling, an electrical coupling and/or a magnetic coupling. In one approach, the coupling can comprise one or more threads that engage complimentary threads of a port 16 of the barrier 15. The coupling and/or the housing 45 can be affixed to (e.g., fixedly mounted on, fixedly attached to) the barrier 15. Alternatively, the coupling and/or the housing 45 can be integrally formed with the barrier 15. The coupling and/or the housing 45 and/or a component of the coupling and/or the housing can alternatively be removably engaged with the barrier 15. In any case, the coupling and/or the housing 45 can comprise one or more components (e.g. circuit modules) that are installed components of the fluidized or nonfluidized bed system, and/or one or more components (e.g., circuit modules) that are components of the ported sensor or ported sensor subassembly and which are functional as coupling components when the ported sensor or ported sensor subassembly are interfaced with the fluidized or nonfluidized bed system.

General Monitoring Applications

The methods and systems and apparatus of the invention can be used to monitor fluidized and nonfluidized systems for various purposes. The inventions can be advantageously used, for example, to monitor particles and multi-phase systems having such particles in any of the following field applications: materials or process research, materials or process development, materials or process quality assurance (QA), process monitoring/evaluation, process control, manufacturing including polymer manufacturing, and service applications involving any of the foregoing.

As described above in connection with the generally preferred approaches, systems, and apparatus (e.g., in connection with FIGS. 1, 2 and 4), the sensor is interfaced with one or more fluidized or nonfluidized bed systems. The sensor is operational for monitoring a property of a fluid within the fluidized or nonfluidized bed system. The fluid property can be monitored in real time, in near real time, or in time-delayed modes of operation.

Further details of preferred fluidized and nonfluidized systems, particles and multi-phase systems containing particles, properties, sensors and monitoring, including specific methodology approaches and apparatus features thereof are described herein (above and below), and each of the herein-described details are specifically considered in various combinations and permutations with the generally described aspects in this subsection of the specification.

Monitoring of Fluidized and Nonfluidized Systems—Invention-Specific Considerations Monitored Property/Properties In the methods and systems and apparatus of the invention, the particular property being monitored is not narrowly critical. In general, the property of interest will depend on the particle and the significance of the monitoring with respect to a particular fluidized or nonfluidized system in a particular commercial application. The property being monitored for a particular fluidized or nonfluidized system may also depend to some extent on the type of sensor. Significantly, some properties of solids and multi-phase systems including solids are of general importance across a wide range of commercial applications. For example, the localized density and mixing factor of a multi-phase system is of near universal interest for many fluidized and nonfluidized bed systems. Likewise, the granular temperature and elastic modulus of particles is also of great general interest for many fluidized and nonfluidized bed systems. It is especially advantageous to be able to monitor properties of particles and multi-phase systems of which they are a part—based on the same monitoring event (e.g., concurrently or simultaneously, using the same sensing element). Significantly, flexural resonators such as tuning forks, unimorphs (e.g., disc benders), bimorphs, torsional resonators, etc. have been demonstrated by Matsiev et al. to have the capability of concurrent or simultaneous monitoring of both viscosity and density in fluidic systems. See Matsiev, "*Application of Flexural Mechanical Resonators to Simultaneous Measurements of Liquid Density and Viscosity*," IEEE International Ultrasonics Symposium, Oct. 17-20, 1999, Lake Tahoe, Nev., which is incorporated by reference herein for all purposes, and see also U.S. Pat. Nos. 6,401,519; 6,393,895; 6,336,353; 6,182,499; 6,494,079 and EP 0943091 B1, each of which are incorporated by reference herein for all purposes. These teachings are herein extended to allow characterization of particles and multi-phase systems including solid particles and a gaseous continuous phase.

In any of the approaches described herein (above and below), the response of the sensor may be caused by the impact of the particles against the sensor alone in a fluidized bed (passive mode), by a combination of the impact of the particles and an external stimulus in a fluidized bed (active mode), or as a result of an external stimulus in a nonfluidized bed (active mode). Further, where multiple sensors are present at different positions along the barrier and/or in the bed, the sensor responses may be used to determine relative measurements. For example, the responses of sensors 40-1 and 40-3 of FIG. 2 can indicate a relative granular temperature of particles at the bottom of the reaction zone to those at the top of the reaction zone without the need to quantify the data.

In one approach, a localized density in an area surrounding the sensor in a fluidized or nonfluidized bed is measured. In a fluidized and nonfluidized bed system, the localized density preferably refers to the mass, number or volume of particles in a given unit volume of the multi-phase system of which the particles are a part. In one preferred embodiment, the response of the mechanical resonator sensor is compared to a set of experimental data to determine the localized density of the multi-phase system. The calculation may take into account such variants as accumulation on the sensor surface, this being detectable as described below; an effect on the sensor due to the current elastic modulus or granular temperature of the particles, etc. In general, greater particle density causes a downward shift in the peak resonant frequency of the mechanical resonator sensor. Also, the presence of many particles around the tines absorbs resonant energy from the fork, attenuating the amplitude of its oscillations.

In one approach, a granular temperature of the particles is determined. In general, the granular temperature is a measure of the kinetic energy associated with the random velocity fluctuations due to collisions between particles. The granular temperature should not be confused with the thermal temperature of the particles. A gas-solid multi-phase system is a collection of a large number of discrete solid particles in a gaseous environment. In a fluidized bed, instead of moving in blocks of particles, each particle moves freely except for quasi-instantaneous collisions with other particles. In this regime, the velocity of each particle can be decomposed into a sum of the mean velocity of the bulk material and an apparently random component. The mean square value of the random velocities is referred to as the "granular temperature," by analogy between the random motion of the granular particles and the thermal motion of molecules in a gas. FIG. 8E and related description describe illustrative methods to measure granular temperature.

In one approach, a mixing factor of the particles in a bed is determined. The mixing factor in one embodiment refers to the fluidization state of the particles in the vicinity of the sensor. In one preferred embodiment, the response of the mechanical resonator sensor is compared to a set of experimental data to determine the mixing factor of the multi-phase system. In another embodiment, the responses of the sensor are compared to historical data to determine a variation in the mixing factor. FIGS. 8E, 12-17 and related description describe illustrative methods to measure a mixing factor of the particles in a multi-phase system in a fluidized bed.

In one approach, an elastic modulus of the particles in a bed is determined. Plasticization of polymers particles, as indicated by an decrease in the elastic modulus of the particles, is often a precursor to the agglomeration of particles into large chunks that can adversely affect the dynamics of the fluidized bed as well as potentially plug the product outlet port. A more significant problem caused by plasticization is accumulation of particles on the available surfaces within the barriers of the system. This not only affects the performance of sensors, but more drastically, may cause sheeting. FIG. 8F and related description describe illustrative methods to determine an elastic modulus of the particles in a multi-phase system.

In one approach, one or more particle-motion properties of the particles in a bed are determined. These properties quantify or otherwise indicate a quality or extent of particle motion. One particularly useful particle-motion property is average momentum of the particles in the bed. In a fluidized bed, for example, the average momentum can be used to characterize the extent of agitation in the bed. In a moving bed, the average momentum can be used to determine changes in or a rate of flow of the particles through a vessel.

Other properties can also be of interest, alternatively to or in addition to the aforementioned properties. For example, temperature and/or pressure and/or flow rate are similarly of near-universal interest across a wide range of commercial applications. Parallel resistance can also be of interest. One or more mechanical resonator sensors and/or other types of sensors (e.g., thermocouples, etc.) can be provided to individually or complementarily measure some or all of the properties and parameters mentioned herein.

Another beneficial measurement is that of a height of a fluidized bed. Because the sensor response is indicative of impacts of particles thereagainst, the frequency of impacts can be used to readily approximate the height of the fluidized bed at any given time. For example, by observing the responses of sensors 40-1, 40-2 and 40-3 of FIG. 2, one can readily estimate a level of the fluidized bed in the reactor 110. Similarly, the presence of any condensed liquid in portions of the fluidized bed polymerization reactor can also be determined by monitoring the responses of the sensors in those locations.

The various properties and other measurable parameters described above and below are useful for characterizing the state of a fluidized bed and the particles therein, and can further be used to: anticipate collapse of the bed, determine initiation of fluidization, determine uniformity of fluidization (presence and extent of channeling, slugging, etc. e.g., based on mixing factor), determine a probability or actual occurrence of agglomeration or sheeting (e.g., based on elastic modulus and/or granular density), determine a rate of reaction (as in batch reactor systems), determine an extent of reaction (particularly in batch reactor systems), etc.

Sensing Operations

The interfaced sensor can be advantageously applied to sense the particles in fluidized and nonfluidized beds by collecting data, and typically a data stream that is dependent upon the bed and particle type, and that can be processed to identify and evaluate particular property characteristics of the particles and multi-phase systems in the beds.

In any of the aforementioned and/or following-mentioned approaches and embodiments, the signal processing circuitry can comprise one or more circuit modules for processing data originating from the sensing element (generally, directly or indirectly). The signal processing circuitry can comprise each such circuit module alone (i.e., individually) or in various combinations and permutations. The data being processed can be raw data (previously unprocessed data) typically coming either directly from the sensing element or from a data storage media (i.e., data memory circuitry) that captured the data directly from the sensing element. Alternatively, the data being processed by one or more circuit modules of the signal processing circuit can be previously processed data (e.g., from another module thereof).

Figure 5A:
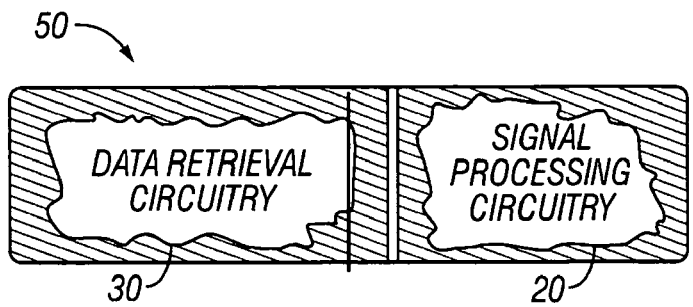
FIGS. 5A through 5C are schematic representations of a processing unit comprising signal processing circuitry and/or data retrieval circuitry.
Figure 5B:
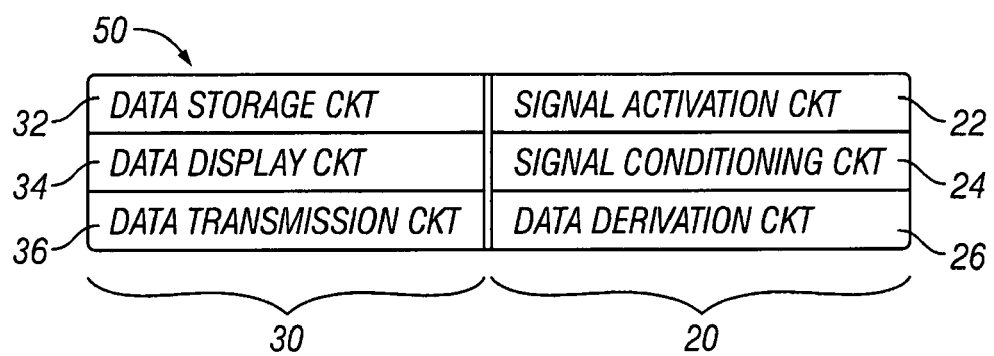

Generally, referring now to FIGS. 5A and 5B, the signal processing circuit 20 can comprise one or more circuits (or circuit modules) for activating a sensing element and/or for processing data originating with a sensing element, including generally for example: a signal activation circuit 22 (generally optional, e.g., for providing an electronic stimulus to the sensing element during active sensing, as discussed in more detail below); a signal conditioning circuit 24 for processing data originating from the sensing element (generally preferred, e.g., for altering an electronic characteristic of a data signal, typically resulting in a conditioned data or data stream); and/or a data derivation circuit 26 for processing data originating from the sensing element (generally preferred, e.g., for identifying, selecting or interpreting a particular electronic characteristic of a data signal, typically resulting in derived data or data stream that is more closely related to the property (or properties) of interest (e.g., has higher information content and/or greater information value) than a raw data stream and/or a conditioned data or data stream).

Figure 5C:
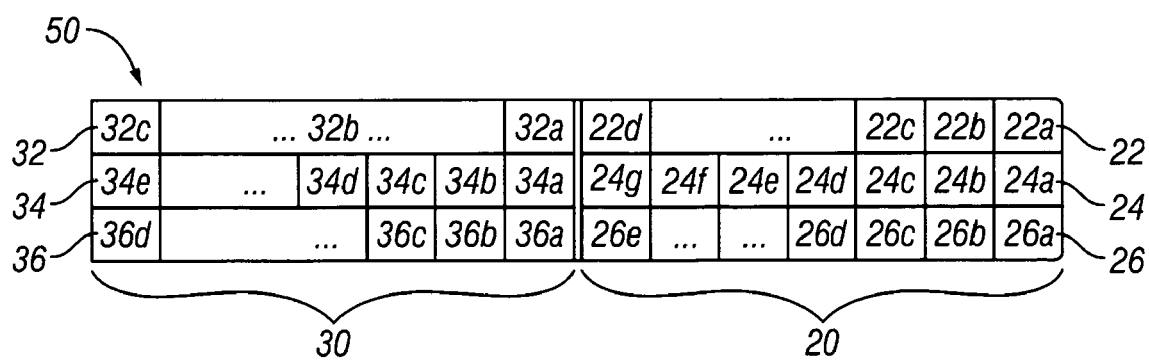

In particular, with further reference to FIG. 5C, the signal processing circuit 20 can comprise one or more circuits (or circuit modules) as signal conditioning circuits 24, such as for example: signal input circuitry 24a (e.g., for receiving a response signal from the sensing element); amplifying circuitry 24b (e.g. including pre-amplifiers and amplifiers, for amplifying a signal); biasing circuitry 24c (e.g., for offsetting or otherwise changing a reference frame relating to the signal, including such as for reducing analog signal offsets in the response signal); converting circuitry 24d (e.g., analog-to-digital (A/D) converting circuitry for digitizing data or a data stream); microprocessor circuitry 24e (e.g., for microprocessing operations involving data originating from the sensing element and/or user-defined data); signal-processing memory 24f (e.g., typically being accessible to one or more signal processing circuits or circuit modules for providing data thereto, such as for example system-specific and/or sensing-element-specific identifying indicia, user-defined data for signal conditioning, etc.); and/or signal output circuitry 24g (e.g., for outputting a conditioned signal to another circuit module e.g., to a data derivation circuit and/or to a data retrieval circuit).

Referring again to FIG. 5C, the signal processing circuit 20 can comprise one or more circuits (or circuit modules) as data derivation circuits 26, such as for example: signal input circuitry 26a (e.g., for receiving a response signal from the sensing element or from one or more data conditioning circuits 24); signal detection circuitry 26b (e.g., for identifying and/or detecting one or both of phase data and/or amplitude data and/or frequency data of the response signal); microprocessor circuitry 26c (e.g., for microprocessing operations involving data originating from the sensing element, typically involving a microprocessor configured for processing one or more software operations such as software algorithms or firmware algorithms (e.g., a data-fitting algorithm) for determining a parameter of the fluid that is associated with a property thereof, and/or typically for processing user-defined data (e.g., predefined data and/or substantially concurrently-defined data) in conjunction with the data originating from the sensing element, and/or typically involving user-initiated, user-controllable, and/or user-interactable processing protocols, typically for determining a parameter using a calibration with a fitting algorithm, for determining a parameter using a correlation algorithm, for determining a change in a detected signal characteristic (e.g., frequency, amplitude) or for determining a determined parameter); signal-processing memory 26d (e.g., typically including electronic data storage media, such as non-volatile memory (e.g., ROM, PROM, EE-PROM, FLASH memory, etc.), typically being preloaded with and/or being accessible for loading user-defined data (e.g., calibration data, correlation data, data defining approximated fluid properties, system-specific information, sensing-element specific information such as an identifying indicia, and/or typically being accessible to one or more signal processing circuits (or circuit modules) for use thereof; and/or signal output circuitry 26e (e.g., for outputting a conditioned signal to another circuit module (e.g., to a data derivation circuit and/or to a data retrieval circuit).

Likewise, in any of the aforementioned and/or following mentioned approaches and embodiments, referring again to FIGS. 5A and 5B, the data retrieval circuitry 30 can comprise one or more modules for retrieving data—whether raw data or processed data. Generally, the data retrieval circuit 30 can comprise one or more circuits (or circuit modules), including a data storage circuit 32, a data display circuitry 34 and/or a data transmission circuitry 36. The data retrieval circuit 30 can be in electrical communication with the sensing element directly, or alternatively, via a signal processing circuit 20 that processes (e.g., amplifies, biases, converts, etc.) raw data coming from the sensing element.

With further reference to FIG. 5C, the data storage circuit 32 can typically comprise: signal input circuitry 32a (e.g., for receiving raw data or a raw data stream from the sensing element, and/or for receiving conditioned data or a conditioned data stream from one or more data conditioning circuits 24, and/or for receiving derived data or a derived data stream from one or more data derivation circuits 26); a data storage media 32b (e.g., such as non-volatile memory (e.g., ROM, PROM, EE-PROM, FLASH memory etc.); and, signal output circuitry 32c (e.g., for outputting a stored data or stored data stream to another circuit module (e.g., to a data derivation circuit and/or to a data transmission circuit and/or to a data display circuit).

Data display circuit 34 as shown in FIG. 5C can be configured to be effective for displaying data associated with one or more properties of a fluid, or for displaying a status of the fluid, where such status is based on data associated with a property of the fluid. Hence, data display circuit 34 can include a display device, and can typically comprise: signal input circuitry 34a (e.g., for receiving raw data or a raw data stream from the sensing element, and/or for receiving conditioned data or a conditioned data stream from one or more signal conditioning circuits 24, and/or for receiving derived data or a derived data stream from one or more data derivation circuits 26, and/or for receiving stored data or stored data stream from one or more data storage circuits 32); a data-display memory 34b (e.g., such as non-volatile memory (e.g., ROM, PROM, EE-PROM, FLASH memory, etc., or random access memory (RAM), in either case typically for temporarily storing a data or data stream to-be-displayed); a microprocessor circuit 34c (e.g., for processing/modifying data, such as stored, to-be-displayed data); a visual display circuit 34d (e.g., digital computer monitor or screen; e.g., a status light such as a LED status light, e.g., a printer, e.g., an analog meter, e.g., a digital meter, e.g., a printer, e.g., a data-logging display device, e.g., preferably in some embodiments a graphical user interface, etc.); and, signal output circuitry 34e (e.g., for outputting a stored data or stored data stream—such as to another circuit module (e.g., to a data derivation circuit and/or to a data transmission circuit and/or to a data display circuit).

Data transmission circuit 36 as shown in FIG. 5C can be configured to be effective for transmitting data originating from the sensing element. Specifically, for example, the data transmission circuit 36 can include: signal input circuitry 36a (e.g., for receiving raw data or a raw data stream from the sensing element, and/or for receiving conditioned data or a conditioned data stream from one or more data conditioning circuits 24, and/or for receiving derived data or a derived data stream from one or more data derivation circuits 26, and/or for receiving stored data or stored data stream from one or more data storage circuits 32); an optional microprocessor circuit 36b (e.g. , for processing/modifying data, such as stored, to-be-transmitted data, and/or for controlling data transmission protocols); transmission protocol circuitry 36c (e.g., for effecting and coordinating communication protocols, such as for example a hard-wired interface circuit (e.g., TCP/IP, 4-20 mA, 0-5V, digital output, etc.), or a wireless communication circuit involving an electromagnetic radiation (e.g., such as radio frequency (RF) short range communication protocols (e.g., Bluetooth™, WiFi-IEEE Standard 80211 et seq., radio modem), land-based packet relay protocols, satellite-based packet relay protocols, cellular telephone, fiber optic, microwave, ultra-violet and/or infrared protocols), or a wireless communication circuit involving magnetic fields (e.g., magnetic induction circuits); and signal output circuitry 36d (e.g., for outputting a transmission of stored data or stored data stream—such as to another circuit module (e.g., to a data derivation circuit and/or to a data storage circuit and/or to a data display circuit).

Data transmission is particularly preferred using a data transmission circuit 36 in connection with a ported sensor subassembly that comprises a signal-processing memory and the data transmission circuit. Where the signal-processing memory comprises user-defined data, such data can be configured to be accessible to the data transmission circuit for communicating the user-defined data from the ported sensor subassembly to the fluidized or nonfluidized bed system or to a remote data repository. In another preferred approach, the ported sensor subassembly can comprise a data transmission circuit for communicating data associated with one or more properties of the particles in the fluidized or nonfluidized bed from ported sensor subassembly to the fluidized or nonfluidized system or to a remote data repository. In another method, the ported sensor subassembly can comprise a data storage media accessible for storing data associated with one or more properties of the fluid, and in combination therewith, a data transmission circuit for communicating stored data from the data storage media to the fluidized or nonfluidized system or to a remote data repository, in either case preferably using a wireless communication protocol.

In any event, preferably, generated data is stored (e.g., in memory), displayed (e.g., in a graphical user interface or other display device) or (meaning additionally or alternatively) transmitted (e.g., using hard-wired or wireless communications protocols) using the data retrieval circuit of the interfaced sensor.

Although listed and represented in the figures in a particular (e.g., linear) order, the invention is not limited to use of such circuit modules in any particular order or configuration, and a person of ordinary skill in the art can determine a suitable circuit design for a particular fluidized or nonfluidized bed system and a particular sensor, in view of the general and specific teaching provided herein.

Active/Passive Sensing Operations

Regardless of the particular configuration for the interfaced sensor, the multi-phase system including the particles can be sensed, actively or passively, using the interfaced sensor during a first sensing period to generate data associated with one or more properties of the fluid. In a passive sensing mode of operation, the flexural resonator sensing element is displaced by the particles impacting thereagainst to generate a signal (e.g., such signal being generated by piezoelectric material of the sensing element, with appropriate electrodes), without application of an electronic input stimulus to the mechanical resonator. In an active sensing mode of operation, an electronic stimulus (e.g., input signal having a voltage and/or frequency) is provided to the flexural resonator sensing element to initiate (via piezoelectric properties) a mechanical response in the sensing element such that at least a portion of the sensing surface of the resonator displaces at least some of the particles in a nonfluidized bed. The mechanical response in a fluidized bed is dependent on the movement, character and quantity of the particles in contact with the sensor, and the extent of that dependence can be measured electronically. With further reference to FIGS. 5B and 5C, a signal activation circuit 22 can comprise, for an active sensing mode of operation, a signal input circuitry 22a (e.g., for receiving a data or a data stream or instructions on active sensing signals) one or more user-defined or user-selectable signal generators, such as a frequency generator circuitry 22b, and/or such as a voltage spike generator circuitry 22c, and in each case, e.g., for providing an electronic stimulus to the sensing element, in an active sensing configuration; and signal output circuitry 22d.

In a preferred operation involving an active sensing mode, a stimulus signal (e.g., such as a variable frequency signal or a spike signal) can be intermittently or continuously generated and provided to the sensing element. A property-influenced signal, such as a frequency response, is returned from the sensing element. The return signal (e.g., frequency response) can be conditioned and components of the signal (e.g., frequency response) can be detected. The method can further include converting the frequency response to digital form, such that the digital form is representative of the frequency response received from the sensing element. Then, first calibration variables can be fetched from a memory. As used herein, the term "fetch" should be understood to include any method or technique used for obtaining data from a memory device. Depending on the particular type of memory, the addressing will be tailored to allow access of the particular stored data of interest. The first calibration variables can define physical characteristics of the sensor or sensing element. Second calibration variables can also be fetched from memory. The second calibration variables define characteristics of the sensor or sensing element in a known multi-phase system. The digital form is then processed when the sensing element is in the particles or multi-phase system under-test, and the processing uses the fetched first and second calibration variables to implement a fitting algorithm to produce data that relates to the properties or characteristics of the particles or multi-phase system under-test.

In some embodiments involving an active sensing mode and using a mechanical resonator sensing element (such as a flexural resonator sensing element), it may be preferable to employ an active sensing mode of operation involving an input stimulus signal having a frequency of not more than about 1 MHz, and preferably not more than about 500 kHz, and preferably not more than about 200 kHz, and most preferably not more than about 100 kHz. In some embodiments, even lower frequencies can be employed in the operation of the mechanical resonator sensing element, including for example frequencies of not more than about 75 kHz. Specific operational ranges include frequencies ranging from about 1 kHz to about 1 MHz, preferably from about 1 kHz to about 500 kHz, preferably from about 1 kHz to about 200 kHz, preferably from about 1 kHz to about 100 kHz, preferably from about 1 kHz to about 75 kHz, more preferably from about 1 kHz to about 50 kHz, more preferably still from about 5 kHz to about 40 kHz, even more preferably from about 10 kHz to about 30 kHz and most preferably from about 20 kHz to about 35 kHz. In such embodiments, it may be preferable to provide an input stimulus signal that has a frequency that varies over time. In such embodiments, it may be preferable to provide two or more cycles of varying a frequency over time over a predetermined range of frequencies, and preferably over a frequency range that includes the resonant frequency for the flexural resonator sensing element. Such frequency sweeping offers operational advantages that are known in the art.

In a preferred operation involving a passive sensing mode, the sensing element, preferably a mechanical resonator such as a flexural resonator, interacts with the particles to generate a property-influenced signal. The signal from the sensing element is intermittently or continuously observed and/or retrieved by the signal processing circuit. The signal can be conditioned and components of the signal (e.g., frequency response, voltage, etc.) can be detected. The method can further include converting the response to digital form, such that the digital form is representative of the signal received from the sensor. Then, as above in the active mode, first and/or second calibration variables can be fetched from a memory. The first calibration variables can define physical characteristics of the sensor or sensing element. Second calibration variables can also be fetched from memory. The second calibration variables can define characteristics of the sensor or sensing element in a known multi-phase system. The digital form can then be processed when the sensing element is in the multi-phase system under-test, and the processing uses the fetched first and second calibration variables to implement a fitting algorithm to produce data that relates to the properties or characteristics of the particles or multi-phase system under-test.

In preferred embodiments, one or more circuit modules of the signal processing circuit and/or the data retrieval circuit can be implemented and realized as an application specific integrated circuit (ASIC). See, for example, above-referenced U.S. Ser. No. 10/394,543 entitled "Application Specific Integrated Circuitry For Controlling Analysis For a Fluid" filed on Mar. 21, 2003 by Kolosov et al., and now U.S. Pat. No. 6,873,916, and PCT Application. No. PCT/US2004/008555 entitled "Application Specific Integrated Circuitry For Controlling Analysis For a Fluid" filed on Mar. 19, 2004 by Kolosov et al. Particularly preferred circuit configurations are described below, but should be considered generally applicable to each approach and embodiment of the inventions described herein.

User-Defined Data (E.G., Calibration, Identifying Indicia)

Generally relevant to each of the methods, systems and apparatus of the embodiments described below and above, user-defined data such as calibration data, correlation data and signal-conditioning data can be employed as part of a signal processing circuit (e.g., signal conditioning and/or data derivation circuitry). Likewise, additionally or alternatively, identifying indicia such as bar-codes, electronic signatures (e.g., 64-bit serial numbers) can be used to identify one or more of: particular fluidic systems, particular locations within a fluidic system; particular fluid types; particular sensors; and/or particular sensing elements (including sensing element types (e.g., tuning fork flexural resonator), sensing element lot numbers for a set of co-manufactured sensing elements, and specific particular individual sensing elements). Such user-defined identifying indicia can be particularly useful in combination with user-defined calibration, correlation and/or signal conditioning data since such data can be specific to the fluidic system, the location, the fluid type; the sensor (type or individual sensor) and/or the particular sensing elements (including sensing element types (e.g., tuning fork flexural resonator), sensing element lot numbers for a set of co-manufactured sensing elements, and specific particular individual sensing elements). The user-defined data can be particle-property (e.g., temperature) dependent, and therefore, there can be interaction between one or more sensing elements (e.g., temperature sensing element) and a user-defined data (e.g., calibration data) for a particular fluid in a particular system using a particular resonator. The user-defined data can generally be pre-defined data or can be concurrently-defined data, and the defining can be done by a person and/or by a computer.

The level of specificity of any particular user-defined data to any particular fluidic system, fluid, sensor or sensor element will depend on the particular user-application, the property of interest, the sensor type, the required degree of accuracy, etc.

In a preferred methods, apparatus and systems, in which a flexural resonator sensing element is employed alone or in conjunction with one or more other systems, it is preferable to have accessible user-defined calibration data that includes at least (i) flexural resonator sensing element-specific (e.g., calibration) data, as well as (ii) application-specific data (e.g., calibration data). It is also preferable to have specific user-defined identifying indicia.

Other variations on this approach can likewise be beneficially applied.

Sensors Having Flexural Resonator Sensing Elements and Operation Thereof

Figure 6:
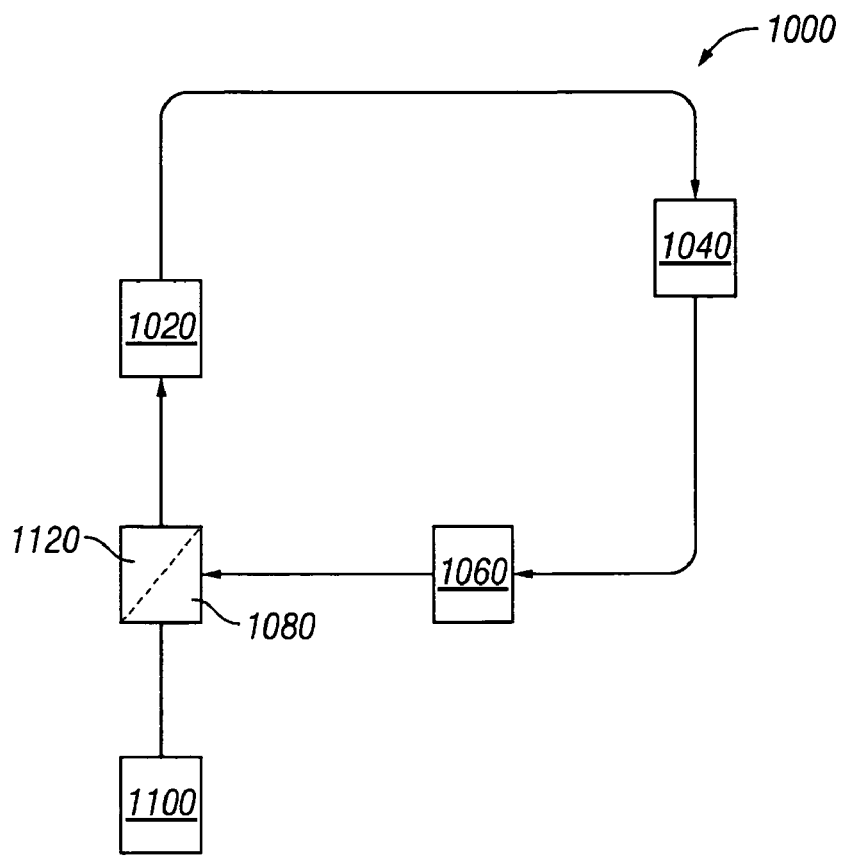
FIG. 6 is a schematic representation of a fluidic system.

As seen in FIG. 6, one embodiment involves the incorporation of a sensor according to the present invention into a fluidized or nonfluidized bed system 1000, such as a fluidized bed polymerization reactor, that includes one or more unit operation devices 1020, 1040, 1060 such as a compressor, an expansion valve, a condenser and an evaporator through which a fluidizing gas can be cycled via one or more passages, such as in a conduit. Other components may also be employed as desired, such as one or more suitable pumps, a filter, a dryer, a suitable flow cell, the components of the reactor systems shown in FIGS. 2 and 4, or a combination of two or more thereof. Likewise, any of the above components may be omitted from a system of the present invention. Suitable valving and process monitoring instrumentation may also be employed in the fluidized bed system 1000.

One or more of the interfaced sensors 1080 according to the present invention is adapted for permanent or temporary placement within in one of the system components or between one of the system components. For example one or more sensors 1080 may be situated between various unit operation devices 1020, 1040, 1060. Likewise, one or more interfaced sensors may additionally or alternatively be incorporated in another component, such as a conduit, coil, filter, nozzle, dryer, pump, valve or other component, or positioned upstream or downstream therefrom. The sensor may be located in the flow path of the fluid (e.g., in a conduit), a headspace or both. In a particular embodiment, the sensor is included along with (and optionally integrated therewith) a condition monitoring device such as a temperature measurement device, a pressure measurement device, a mass flow meter, or combinations of two or more of such devices. Without limitation, an example of a combined pressure and temperature sensor is discussed in U.S. Pat. No. 5,586,445 (incorporated by reference).

Optionally, the interfaced sensor, the ported sensor subassembly, or the ported sensor can be in signaling communication with a processing unit 1100 (which may include a user interface) for controlling operation of the system 1000. The processing unit 1110 may be microprocessor integrated into the ported sensor, the ported sensor subassembly or the interfaced sensor, for example, as part of the signal processing circuitry as described above. The processing unit 1100 can optionally also be in signaling communication with a condition monitoring device 1120 (shown as part of an integrated assembly with the interfaced sensor 1080). Thus, data obtained from the interfaced sensor 1080 may be processed along with other data to assist in monitoring and establishing operating conditions of the system 1000.

Thus, for example, in one aspect of the present embodiment, an interfaced sensor 1080 according to the present invention is employed to monitor at least one property of a multi-phase system (e.g., the simultaneous monitoring of granular temperature, mixing factor, elastic modulus and/or localized density). Data generated from the sensor, along with other data (e.g., temperature, pressure, flow rate, or combinations thereof), for example, from the condition monitoring device 1120, can be sent to the processing unit 1100. From the data provided, the processing unit 1100, which typically will be programmed with a suitable algorithm, will process the data. In a process control embodiment, the processing unit can effect least one operation of the system 1000 selected from switching a subsystem of the system 1000 (e.g., a unit operation device 1020, 1040, 1060) or one or more components thereof between an "on" or "off" state, partially or fully shutting or opening a valve in the system 1000 (e.g., for varying a flow rate of a fluidizing fluid, monomer, catalyst, recycle flow rate, condensing agent, static control agent, sheeting control agent), controlling a rate of heat removal from a reactor vessel (such as by increasing cooling of the fluidizing gas), changing a pressure in the system, changing the operating speed or condition of one or more components of the fluidic system, or otherwise controlling operation of the system 1000 or a component thereof, providing a visual output signal, providing an audible output signal, or a combination thereof.

It will be appreciated that the above configuration of FIG. 6 permits the use of one or more modes of active sensing operations, such as excitation at one or more frequencies around resonance frequency of the resonator, or the time decay of oscillation after an electrical or mechanical impulse (e.g., a voltage spike). Passive operations can include, for example, observing passive oscillations due to ambient noise, vibrations, electromagnetic interference, etc.

Figure 7A:
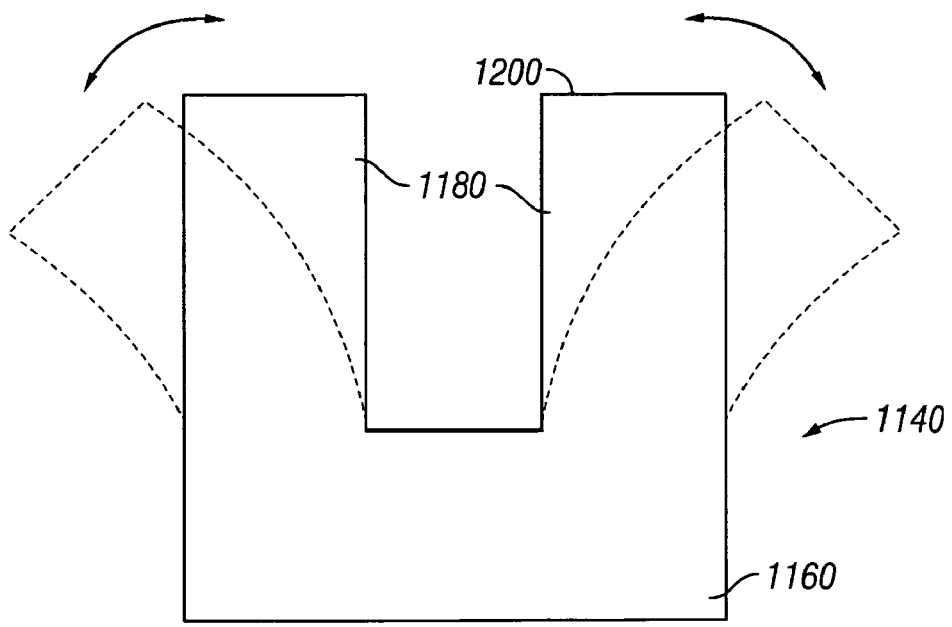
FIGS. 7A through 7H are schematic representations of several configurations for flexural resonator sensing elements.

Turning now to FIG. 7A there is shown an illustration of one preferred resonator element 1140 in accordance with the present invention. The resonator element 1140 preferably includes a base 1160 that has at least two tines 1180 having tips 1200 that project from the base. The shape of the tines and their orientation relative to each other on the base may vary depending upon the particular needs of an application. For example, in one embodiment, the tines 1180 are generally parallel to each other. In another embodiment the tines diverge away from each other as the tips are approached. In yet another embodiment, the tines converge toward each other. The tines may be generally straight, curved, or a combination thereof. They may be of constant cross sectional thickness, of varying thickness progressing along the length of the tine, or a combination thereof.

Resonator sensing element(s) are suitably positioned in an element holder. Alternatively, the elements (with or without a holder) may be securably attached to a wall or barrier or other surface defining one of the fluidic systems or passages into which it is placed. In yet another embodiment, the element is suitably suspended within a passage such as by a wire, screen, or other suitable structure.

Element holders may partially or fully surround the sensing elements as desired. Suitable protective shields, baffles, sheath or the like may also be employed, as desired, for protection of the elements from sudden changes in fluid flow rate, pressure or velocity, electrical or mechanical bombardment or the like to help locate an element relative to a fluid or combinations thereof. It should be appreciated that resonator elements may be fabricated from suitable materials or in a suitable manner such that may be employed to be re-useable or disposable.

Examples of approaches to materials combinations, or the packaging of sensing elements that may be employed in accordance with the present invention are disclosed, without limitation in U.S. Provisional Application Ser. Nos. 60/456,767 and 60/456,517 (both filed Mar. 21, 2003) (and incorporated by reference). Thus, one particular approach contemplates affixing a sensing element having an exposed sensing surface to a platform, wherein a spaced relationship is created between the exposed sensing surface and the platform. A suitable protective layer may be applied to cover the platform and/or the sensing element while maintaining an exposed sensing surface. The latter exposed sensing surface may be prepared by the use of a consumable protective layer (e.g., a polymer, starch, wax, salt or other dissolvable crystal, low melting point metal, a photoresist, or another sacrificial material) that is used to block the exposed sensing surface prior to applying the protective layer.

A plurality of the same type or different types of resonators of resonators can be used in combination. For example, a low frequency resonator may be employed with a high frequency resonator. In this manner, it may be possible to obtain a wider range of responses for a given sample.

The size of the sensing elements, especially mechanical resonator sensing elements such as flexural resonator sensing elements is not critical to the invention. In some applications, however, it should be appreciated that one advantage of the present invention is the ability to fabricate a very small sensor using the present resonators. For example, one preferred resonator has its largest dimension smaller than about 2 cm, and more preferably smaller than about 1 cm. One resonator has length and width dimensions of about 3 mm by 8 mm, and possibly as small as about 1 mm by 2.5 mm. Geometry of the resonator may be varied as desired also. For example, the aspect ratio of tines of the tuning forks, or geometrical factors of other resonators can be optimized in order to achieve better sensitivity to the properties of the gas phase, liquid phase or its particular components (e.g., a lubricant). For example, the aspect ratio of a tuning fork tine may range from about 30:1 to about 1:1. More specifically, it may range from about 15:1 to about 2:1.

Figure 7B:
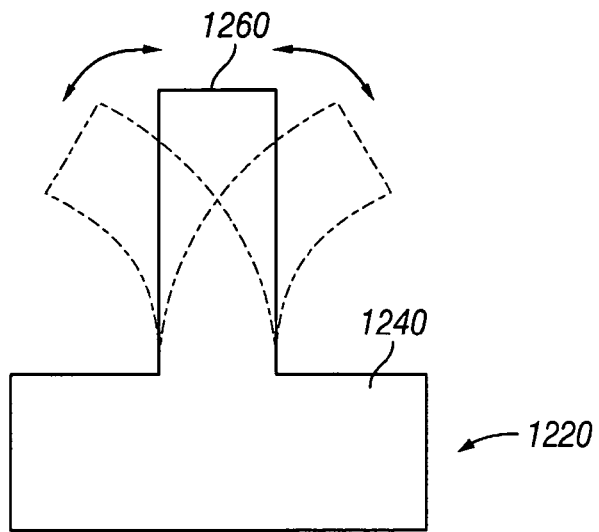
Figure 7C:
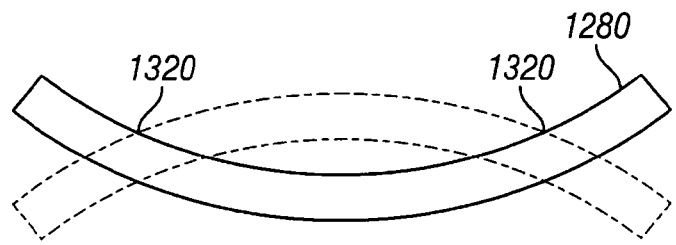
Figure 7D:
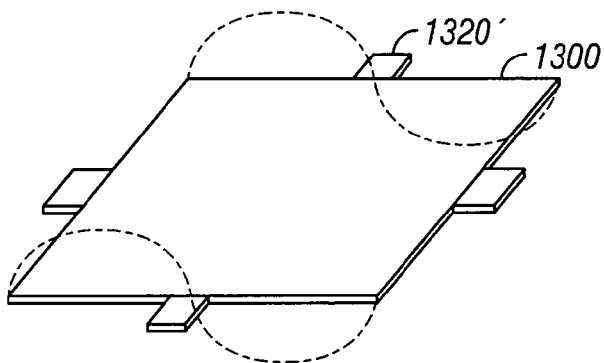
Figure 7E:
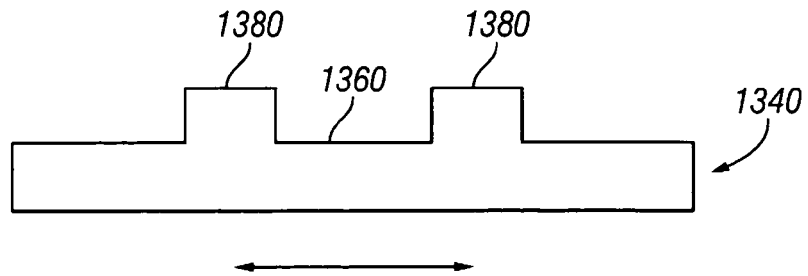

It is thus seen that a preferred resonator is configured for movement of a body through a fluid. Thus, for example, as seen in FIG. 7A, the resonator may have a base and one or a plurality of tines projecting from the base. It is preferred in one aspect that any tine has at least one free tip that is capable of displacement in a fluid relative to the base. FIG. 7B illustrates a cantilever 1220 having a base 1240 and a free tip 1260. Other possible structures, seen in FIGS. 7C and 7D contemplate having a disk 1280, a plate 1300 or the like that is adapted so that one portion of it is displaceable relative to one or more variable or fixed locations 1320 (1320'). As seen in FIG. 7E, in yet another embodiment a resonator 1340 is contemplated in which a shear surface 1360 of the resonator has one or more projections 1380 of a suitable configuration, in order that the resonator may be operated in shear while still functioning consistent with the flexural or torsional resonators of the present invention, by passing the projections through a fluid.

Figure 7F:
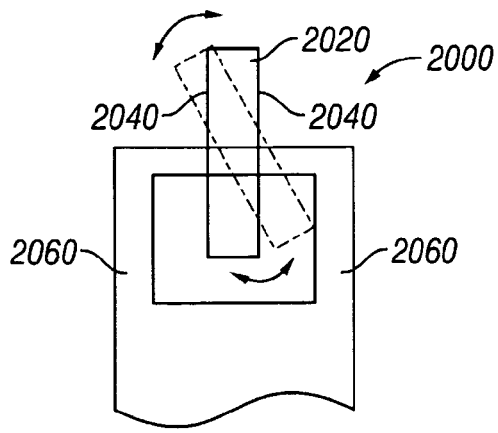
Figure 7G:
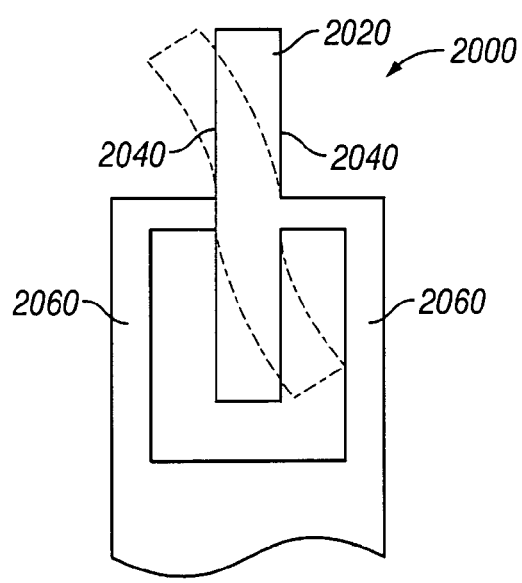
Figure 7H:
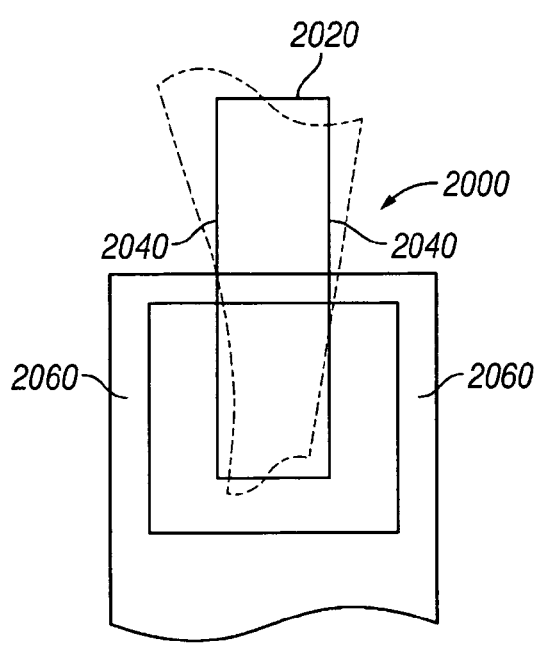

In still other embodiments, and referring to FIGS. 7F, 7G and 7H, it is contemplated that a resonator 2000 may include an elongated member 2020 supported on its sides 2040 by a pair of arms 2060. As shown respectively in FIGS. 7F through 7H, the elongated member may be configured to oscillate side-to-side, back and forth, in twisting motions or combinations thereof.

The flexural resonator, such as the embodiment of FIG. 7B, may be constructed as a monolithic device. Yet another structure of the present invention contemplates the employment of a laminate or other multi-layer body that employs dissimilar materials in each of at least a first layer and a second layer, or a laminate comprised of layers of piezoelectric material of different orientations or configurations. According to this approach, upon subjecting one or more of the layers to a stimulus such as temperature change, an electrical signal or other stimulus, at least one of the materials will respond differently than another and the differences in responses will, in turn, result in the flexure of the resonator. In yet another embodiment, it is contemplated that plural resonators can be assembled together with an electrode at least partially sandwiched therebetween. In this manner, it may be possible to further protect electrodes from harsh conditions, while still achieving the desired flexure. One specific example might include a two or more lithium niobate or quartz tuning forks joined together with a gold electrode therebetween. Other configurations (e.g., an H-shaped resonator) and material combinations may be employed as well, as disclosed in U.S. Provisional Application Ser. Nos. 60/456,767 and 60/456,517 (both filed Mar. 21, 2003), incorporated by reference.

As can be seen, the selection of the specific resonator material, structure, or other characteristic will likely vary depending upon the specific intended application. Nonetheless, it is preferred that for each application, the resonator is such that one or a combination of the following features (and in one highly preferred embodiment, a combination of all features) is present: a coating, if placed upon the resonator in a thickness greater than about 0.1 micron, will not substantially detract from resonance performance; the resonator is operable and is operated at a frequency of less than about 1 MHz, and more preferably less than about 100 $kH_z$; the resonator is substantially resistant to contaminants proximate to the sensor surface; the resonator operates to displace at least a portion of its body through a mass of particles in a nonfluidized bed; or the resonator responses are capable of deconvolution for measuring one or more individual properties of the particles and/or multi-phase system.

The resonator may be uncoated or coated or otherwise surface treated over some or all of its exterior surface. A preferred coating is a metal (e.g., a conductive metal similar to what may be employed for electrodes for the sensor, such as silver, gold, copper, aluminum or the like), plastic, ceramic or composite thereof, in which the coating material is substantially resistant to degradation from the fluid to which it is to be exposed or to surface build-up, over a broad temperature range. For example, one preferred embodiment, contemplates the employment of a base resonator material and a performance-tuning material. Among the preferred characteristics of the resonators of the present invention is the base material is generally thermally stable. For example, in one preferred embodiment, the material exhibits a dielectric constant that is substantially constant over a temperature range of about 0° C. to about 100° C., more preferably about −20° C. to about 150° C., and still more preferably about −40° C. to about 200° C. For example, it is contemplated that a preferred material exhibits stability to a temperature of at least about 300° C., and more preferably at least about 450° C. in order to withstand the heat of reaction in a fluidized bed polymerization reactor vessel. In another aspect, the dielectric constant of the performance-tuning material preferably is greater than that of quartz alone, such as by a factor of 5 or more, more preferably by a factor of 10 or more and still more preferably by a factor of 20 or more.

FIG. 8A illustrates a circuit diagram 11220 for a tuning fork equivalent circuit 11222 and a read-out input impedance circuit 11224. The frequency generator is coupled to the tuning fork equivalent circuit 11222 to a parallel connection of a capacitance Cp as well as a series connection of a capacitor Cs, a resistor Ro, an inductor Lo, and an equivalent impedance $Z(\omega)$. The read-out impedance circuit includes a parallel resistor Rin and a capacitor Cin. The output voltage is thus represented as Vout.

The equations shown in FIG. 8B can define the equivalent circuit. In equation (2), the Vout of the equivalent circuit is defined. In equations (3) and (4), the impedance Zin and Ztf are derived. Equation (5) illustrates the resulting impedance over frequency $Z(\omega)$. As can be appreciated, the voltage Vout, graphed verses the frequency $Z(\omega)$, necessitates the determination of several variables.

The variables are defined in equation (1) of FIG. 8B. In operation, the tuning fork's frequency response near the resonance is used to determine the variables that will define the characteristics of the fluid-under-test. The algorithm that will be used to determine the target fluid under-test characteristic parameters will require knowledge of data obtained during calibration of a tuning fork. In addition to access to calibration data, the algorithm will also utilize a data fitting process to merge approximated variables of the target fluid under-test, to the actual variable characteristics (i.e., density, viscosity, dielectric constant) for the fluid under-test.

In the circuit, it is assumed that Cs, Ro, Lo are equivalent characteristics of a preferred resonator in a vacuum, Cp is the equivalent parallel capacitance in a particular fluid under-test, $\rho$ is the fluid density, $\eta$ is fluid viscosity, $\omega$ is oscillation frequency. Cp is a function of k, as shown in equations (6) through (10). The constant "k" is, in one embodiment, a function of the tuning fork's geometry, and in one embodiment, defines the slope of a curve plotting (Cpmeasured, Cpcal, and Cpvaccum) verses ($\epsilon$measured, $\epsilon$cal, and $\epsilon$vacuum), respectively. In a physical sense, the constant "k" is a function of the tuning fork's geometry, the geometry of the tuning fork's electrode geometry, the tuning fork's packaging (e.g., holder) geometry, the material properties of the tuning fork, or a combination of any of the above factors. The resulting value of Cp will be used to determine the dielectric constant $\epsilon$ as shown by the equations.

Figures 8C, 8D:
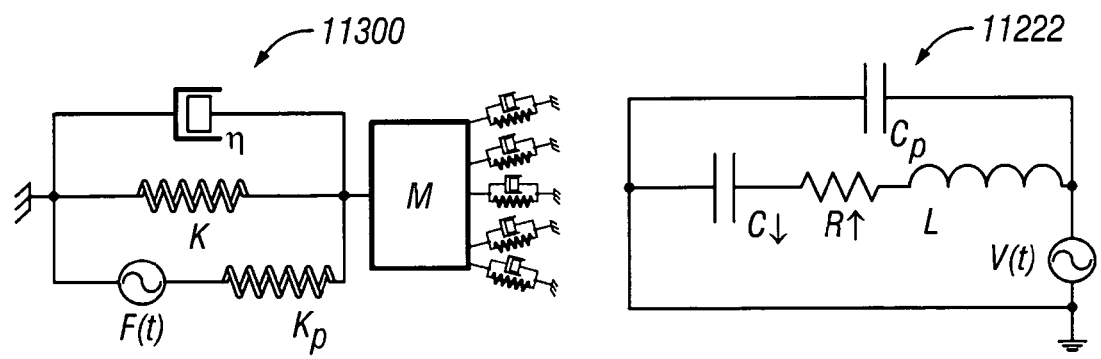
Figure 8E:
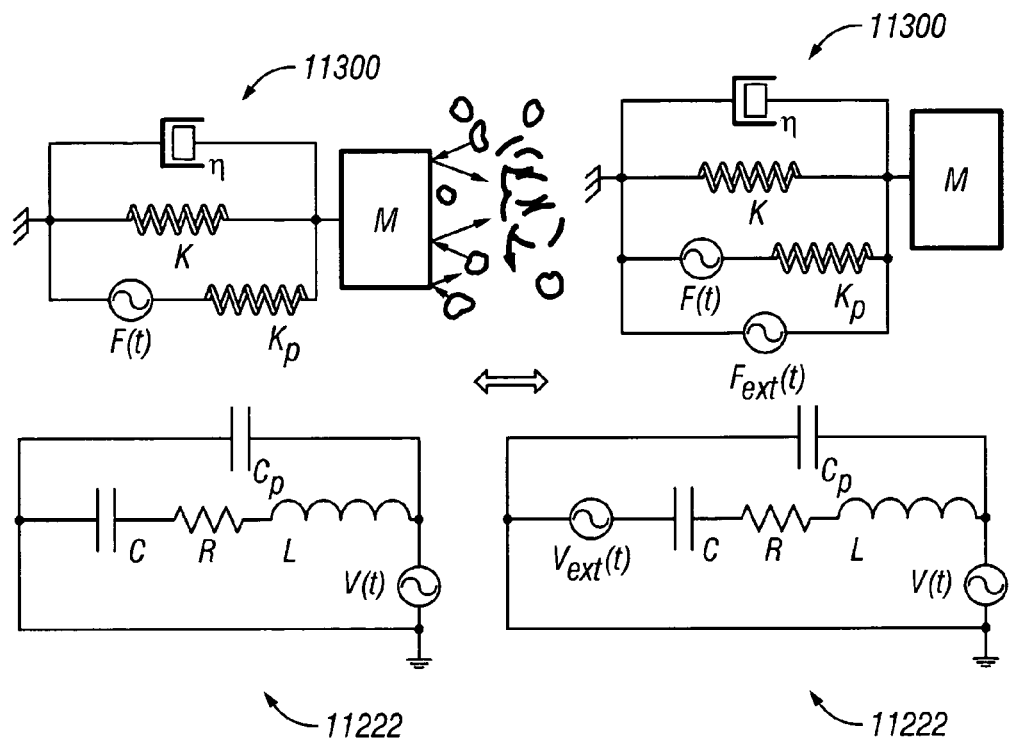
Figure 8F:
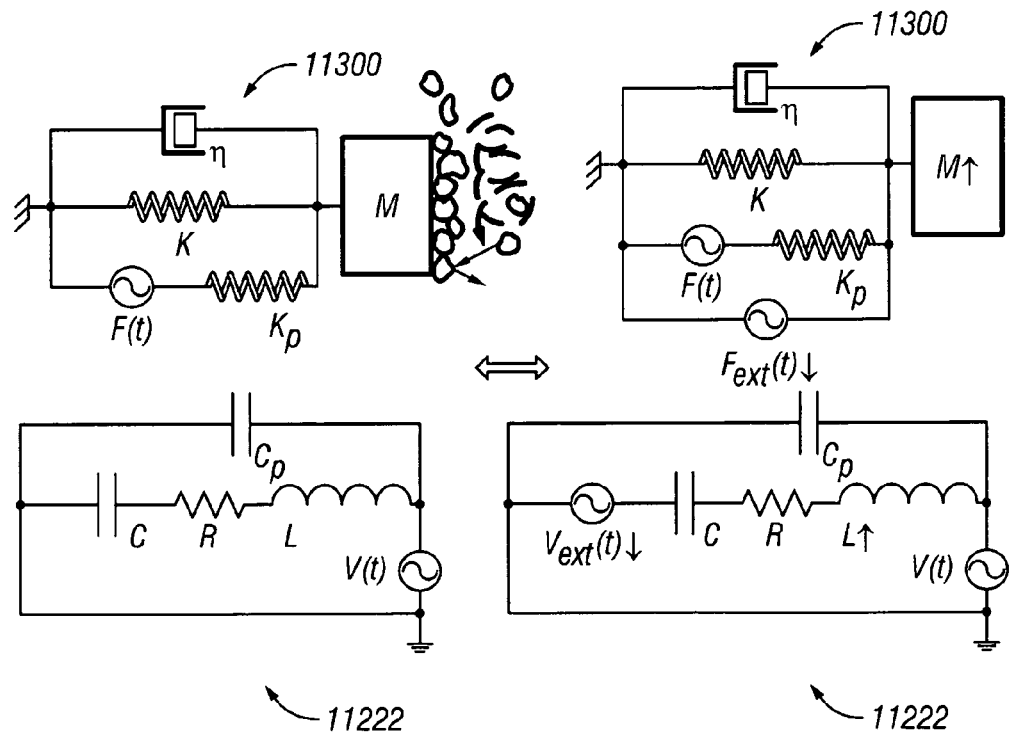

Further, it can be appreciated that that viscosity and density can be de-convoluted based on the equations defined in FIG. 8C. For some sensors, the value of $C_{p\ measured}$ is typically on the order of about 1 to 3 orders of magnitude greater than the value of $C_s$. Accordingly, in order to improve the ability to measure $Z(\omega)$, desirably trimming circuitry is employed as part of or in association with the signal conditioner, such as a trimming circuits. In order to more efficiently process the signal being received from the tuning fork, the signal is signal conditioned to eliminate or reduce the signal offset and thus, increase the dynamic range of the signal produced by the tuning fork. Thus, the data being analyzed can be more accurately processed.

FIG. 8D illustrates the correlation between mechanical and electrical parameters in a nonfluidized bed scenario according to one approach, where the analogies between the electrical circuit 11300 and mechanical circuit 11222 are described in Table 1.

TABLE 1

Analogies among electrical and mechanical circuits

| | Mechanical | | Electrical |
|---|---|---|---|
| F | force | V | voltage |
| X | displacement | q | charge |
| $\eta$ | dashpot (drag, viscous drag) | R | resistance |
| M | mass | L | inductance |
| K | spring constant | C | capacitance |

With continued reference to FIG. 8D, the bed is not fluidized. The particles are compacted around the sensor and not moving at all. Obviously there is no signal from the sensor in passive mode. Energizing the sensor in active mode produces some stress in the surrounding particles without displacing them as the amplitude of oscillations is very low (hundreds of ). Some of that mechanical energy may be lost, i.e., converted into heat, if the particles are lossy, or at least lossier than the monocrystalline LiNbO3 of the sensor according to one embodiment. Therefore the sensor resonant response to the frequency sweep will be damped by the losses in particles and shifted toward higher frequencies as the particles are elastic and adding to the effective stiffness of the sensor. The effects described above can be represented on the diagram as spring-damper pairs attached to the weight M of the resonator. The springs add to the overall strength of the original spring K and the dampers produce additional losses. On the electrical equivalent circuit these effects manifest themselves as a decrease in the capacitance C (inversed stiffness) and increase in the resistance R (energy loss), as shown in FIG. 8D.

Again, since the amplitude of oscillations is very low, the particles do not significantly move with the sensor, and therefore add very little to the effective mass of the sensor and to the inductance on the equivalent circuit. Processing of the resonant curve of the sensor imbedded in stagnant particles allows for quantitative assessing the effects described above.

FIG. 8E illustrates the correlation between mechanical and electrical parameters in a fluidized bed scenario according to one approach. The bed is highly fluidized and violently agitated, the particles are elastic, hard and bouncy. Under these conditions the particles are swirling around the sensor impacting against the sensor surface and each other. Every collision between particle and the sensor produces mechanical energy exchange between the particle and the sensor. The change in particle momentum before and after collision with the sensor surface creates certain external force applied to the sensor according to the equation $F_{ext}=d(mu)dt$, where m is particle mass, u its speed and t is time. The occurrence of particles constantly impacting against the sensor surface creates constantly changing external force applied to the sensor. Turning to the mechanical diagram of FIG. 8E, this force is applied in parallel to the source of electrical excitation and the effective spring $K_p$. Note that the electrical excitation does not necessarily have to be present as the sensor is going to be stimulated, and thus energized, by the collisions with particles. This action is what allows this sensor to work in passive mode. As opposed to the scenario of FIG. 8D, the particles are stressed only at the very instance of the collision and so there is no tangible change to either sensor mass or sensor stiffness.

On the electrical equivalent circuit 11222 of FIG. 8E, the external excitation force manifests itself as an additional voltage source $V_{ext}(t)$ attached in sequence to the mechanical arm of the circuit. Since the current through the sensor can be electronically measured and usually the parameters of the equivalent circuit are known, the $V_{ext}(t)$ can be calculated. This voltage $V_{ext}(t)$ provides a good measure of the granular temperature of the particles as a function of time. Processing of this voltage $V_{ext}(t)$ in the frequency domain allows for distinguishing a "baseline," constant or slowly changing granular temperature as well as fast (e.g., 10 Hz or higher) changes related to the mixing factor or swift changes in local fluidization state.

FIG. 8F illustrates the correlation between mechanical and electrical parameters in a fluidized bed scenario according to one approach. In this example, assume the fluidized bed is exhibiting high to moderate fluidization, and the particles are plasticized and somewhat tacky.

The scenario of FIG. 8F bears certain similarities to the scenario of FIG. 8E, but in this case the momentum exchange between moving particles and the sensor is not as efficient and some particle accumulation on the sensor surface is likely. Theoretically, other conditions equal, the average force produced by the hard elastic particles colliding with the sensor should be twice as high as the force produced by plasticized particles moving at the same average speeds. This effect is readily visible in the substantial decrease in the amplitude of the external force and hence the decrease in the effective voltage source on the equivalent circuit. Thus, by comparing the response of the sensor to a baseline, or against historical data, a decrease in the response voltage of the sensor indicates an increase in elastic modulus or plasticity of the particles.

Plasticization of polymers particles, as indicated by an increase in the elastic modulus of the particles, is often a precursor to the agglomeration of particles into large chunks that can adversely affect the dynamics of the fluidized bed as well as potentially plug the product outlet port. A more significant problem caused by plasticization is accumulation of particles on the available surfaces within the barriers of the system. This not only affects the performance of sensors, but more drastically, may cause sheeting. As opposed to the scenario of FIG. 8D, the particles in this example that have accumulated at the sensor surfaces are moving along with the oscillating mass without being stressed by the sensor. Some very low stress is induced in the particles by inertial forces, but given the low mass of the individual particles, this stress may be barely noticeable. The dominant effect of the particle accumulation is the increase of the overall mass of the oscillating sensor resulting in a decrease in the resonant frequency. The increase of the oscillating mass is reflected as an increase in the equivalent inductance and can be measured by electronic means. This allows for quantitative measurements of the mass attached. Accordingly, because buildup on the sensor can be detected, a probability that sheeting is occurring or about to occur can be determined.

In case of a very substantial build-up, the particles adhered to the sensor might start bridging the notch of the tuning fork. If this happens, the powder in the notch may become stressed by the oscillating tines and therefore the sensor may start demonstrating signs of increasing stiffness that will in turn work against the accumulating mass toward increasing the frequency (as in the scenario of FIG. 8D). The presence of the accumulated mass increases overall mechanical energy stored in the resonator, so the resulting resonant peaks are sharper, while the loss of energy due to stressing lossy material causes the resonance to flatten out. In most cases these two processes can be easily distinguished. Accordingly, because buildup on the sensor can be detected, a probability that sheeting is occurring or about to occur can be determined.

In a fluidized bed system in which particles tend to adhere to the sensor surface, a mechanism to clean the sensor surface may be provided. For instance, a jet of gas may be introduced onto the sensor surface to remove particles adhered thereto. A mechanical arm or brush may wipe or brush accumulated particles from the sensing surface. Additionally, if the sensor is ported, it may be periodically removed for cleaning or replacement. When a cleaning should occur is at the discretion of the operator, and can be readily determined by observing the response of the sensor.

In use in a fluidized bed reactor system for example, the signal being observed will usually show either some combination of all three scenarios (FIGS. 8D-8F) or a transition between them. The scenario of FIG. 8D is indicative of when the powder is stagnant; the scenario of FIG. 8E is indicative of when the bed is highly fluidized, especially if the sensor is placed near the top level of the fluidized bed.

Downstream Data Processing

The methods and systems and apparatus of the invention can be used as described herein to monitor particles and multi-phase systems including particles in fluidized and non-fluidized bed systems to generate data associated with one or more properties of the particles or multi-phase system containing the particles. The data generated can be used directly, for example, as described herein for status evaluation, property logging, property tracking, etc., among other uses. Such data can also be subsequently further processed for further subsequent uses (i.e., downstream) for various purposes. Such downstream processing of the data or data stream (represented for example by a signal or signal stream), typically but not necessarily in connection with other data from other independent sources, can be effectively applied to generate higher level information or knowledge based on the directly generated data, for example for purposes such as one or more of: process monitoring, process control (e.g., involving automated or manual control schemes, such as feedback or feed forward control schemes), reaction enhancement (e.g., adding one more monomers), fluid operating conditions (e.g., temperature, pressure, flowrate, etc.), predictive maintenance (e.g., detecting sheeting and agglomeration), materials or process research, materials or process development, quality control, and maintenance or service applications involving any of the foregoing, among others.

EXAMPLES OF USE AND EXPERIMENTAL DATA

The following description of experimental data is provided by way of example only and is not meant to be limiting.

Application of Tuning Fork Sensor for Detection of Incipient Sheeting by Monitoring Fluidization Near the Wall In the wall region of the fluidized bed of polymer particles, swarms of particles move sporadically in response to bubbles rising near the walls opposing the net downward flow of particles that occurs in this region. Particle velocity at the wall should therefore fluctuate when there is adequate motion to provide the required heat transfer. As adhesion forces start to build relative to the mixing forces imparted by gas and bubble flow, the particle velocity at the wall falls for periods of time, and the velocity fluctuation diminishes. The ability to measure these changes in velocity can help anticipate an impending sheeting condition.

In addition to measuring velocity fluctuations near the wall, one may predict the onset of incipient sheeting by measuring the localized density of particles near the wall. It is believed that particle swarms become more closely packed while motionless, and less closely packed as they move. These localized states can be thought of as dense phase fluidized and lean-phase fluidized (entrained) respectively. The local density should therefore be higher when the particles are motionless and lower when they move. A fluidized bed with good mixing near the wall should therefore show fluctuations in density around the sensor tip, which can be measured with the mechanical resonator sensor. If the bed condition moves toward sheeting, the localized density tends to drift upward and the frequency of fluctuations decreases.

Analysis of Active Mode Data:

Tuning fork measurements were made near the wall in both a 5" inner diameter cold fluidized bed polymerization reactor system model and in a 14" inner diameter cold fluidized bed polymerization reactor system model. Measurements were made as a function of fluidization level from a settled bed in some cases, through minimum fluidization, and up through vigorous slugging fluidization. By scanning gas velocity, the intent was to model the range of fluidization that should occur at the wall in an operating reactor from stable operation through nascent sheeting. Tuning fork sensor signals were analyzed to evaluate whether they could sense the changes in motion and density as described above.

Figure 9:
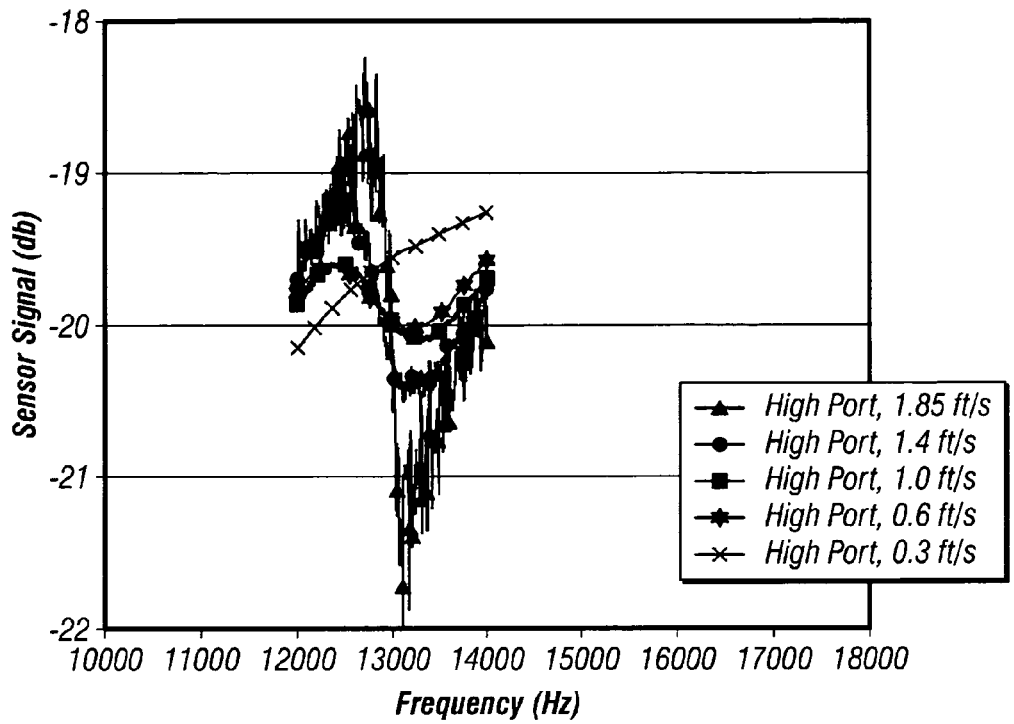
FIG. 9 is a chart depicting an averaged active mode tuning fork sensor response signal as a function of superficial gas velocity, measured at the wall three feet above the distributor plate in the 14" cold fluidized bed polymerization reactor model with high density polyethylene (HDPE).

Averaged active-mode sensor signals as a function of superficial gas velocity, in the 14' cold model are shown in FIG. 9. These were obtained with a high density polyethylene (HDPE) hexane copolymer, with the tuning fork sensor approximately 3 feet above the distributor plate. As can be seen from the figure, the amplitude of the sensor resonance is a function of the gas velocity. The resonant amplitude increases with increasing gas flow because the fork can oscillate more freely in the lower density, less constrained bed; energy transfer to the bed is diminished as bed density decreases. Noteworthy is the fact that the sensor output changes dramatically from the barely fluidized state (0.3 ft/s at this location), and the gentle fluidization state obtained at 0.6 ft/s. Changes like these would be expected in an operating reactor as attractive forces built at the wall and the polymer there becomes defluidized while moving towards becoming a stagnant zone or forming a sheet.

A noteworthy feature is that the resonance curves do not change much as the superficial gas velocity (SGV) is raised from 0.6 to 1.0 ft/s This same observation was made in a number of different data sets. While the cross-sectional voidage must be increasing with the increased flow, the sensor shows that the local voidage and mixing at the wall doesn't change It is clear that at still higher flows, the voidage around the sensor is increasing, perhaps as the sensor spends more and more time in lean-phase bubbles, and so the time-averaged voidage is increasing.

Figure 10:
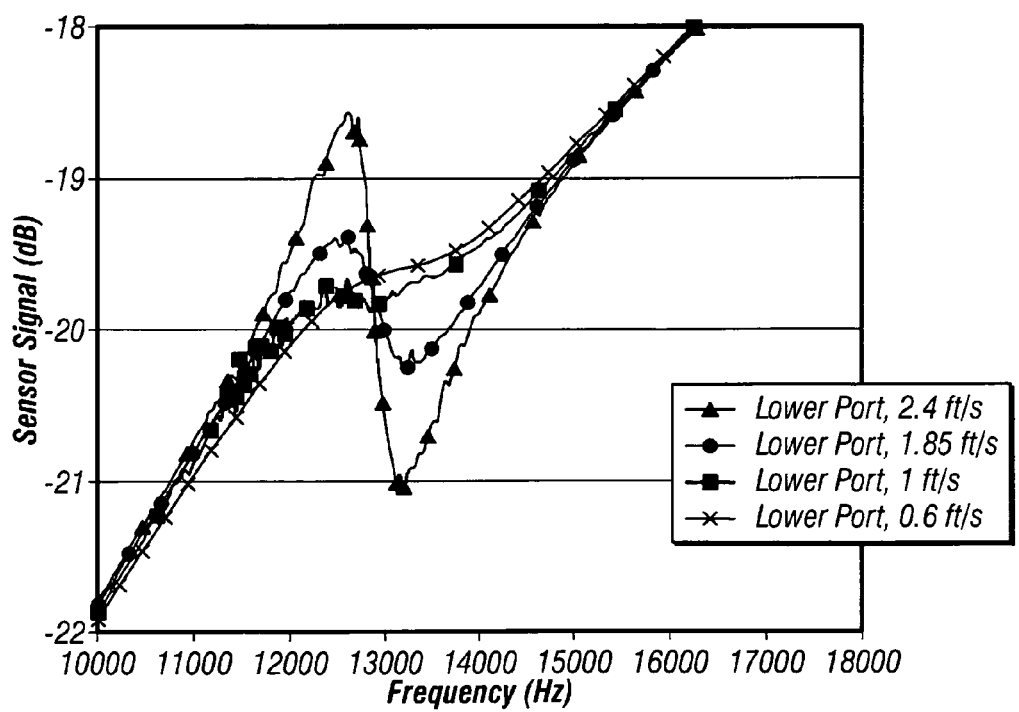
FIG. 10 is a chart of an averaged active mode tuning fork sensor response signal versus superficial gas velocity, measured one foot above the distributor plate in the 14" cold model with HDPE.

Similar traces for points taken with a sensor in a port approximately one foot above the distributor plate are shown in FIG. 10. In comparing the plots of FIGS. 9 and 10, it is apparent that the signal amplitude at a given SGV is significantly reduced in the lower section of the bed where the fluidized bed is denser and there are fewer bubbles and slugs passing the probe. Again, this demonstrates that the sensor response is characteristic of the local environment at the sensor.

Figure 11:
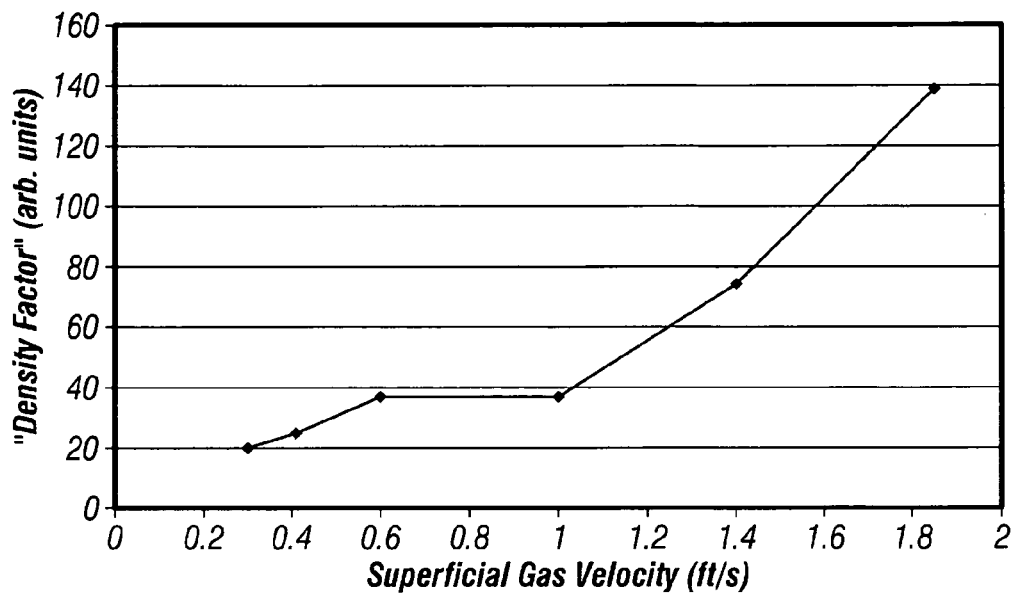
FIG. 11 is a chart reflecting a localized density factor measured from 12-14 kHz as a function of superficial gas velocity, measured ~3 ft above the distributor plate in the 14" cold fluidized bed polymerization reactor model with HDPE.
Figure 12:
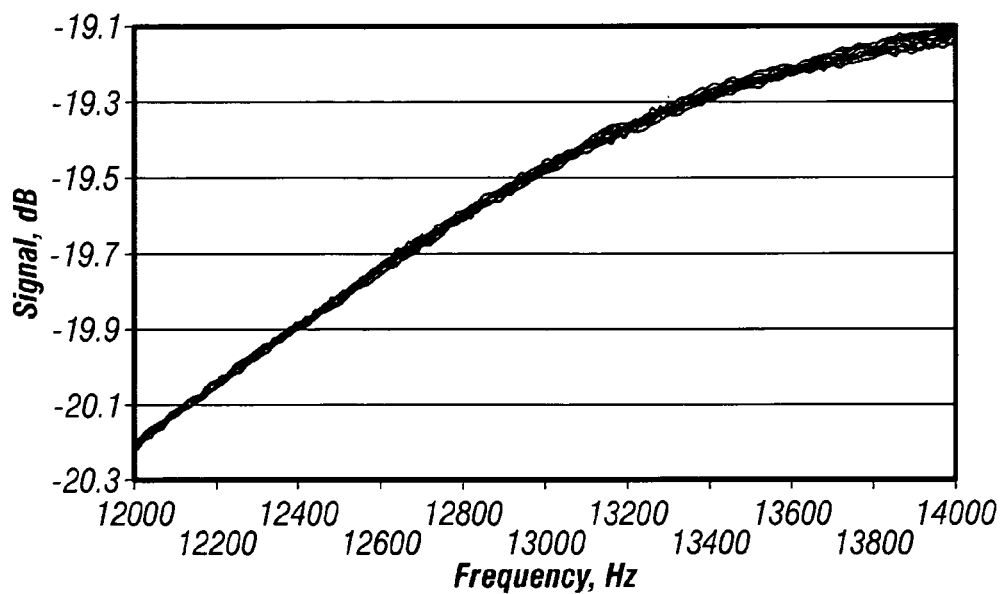
FIG. 12 is a chart reflecting 30 individual sensor frequency sweeps at 0.3 ft/s superficial gas velocity, 3 ft above the distributor plate in the 14" cold fluidized bed polymerization reactor model with HDPE.
Figure 13:
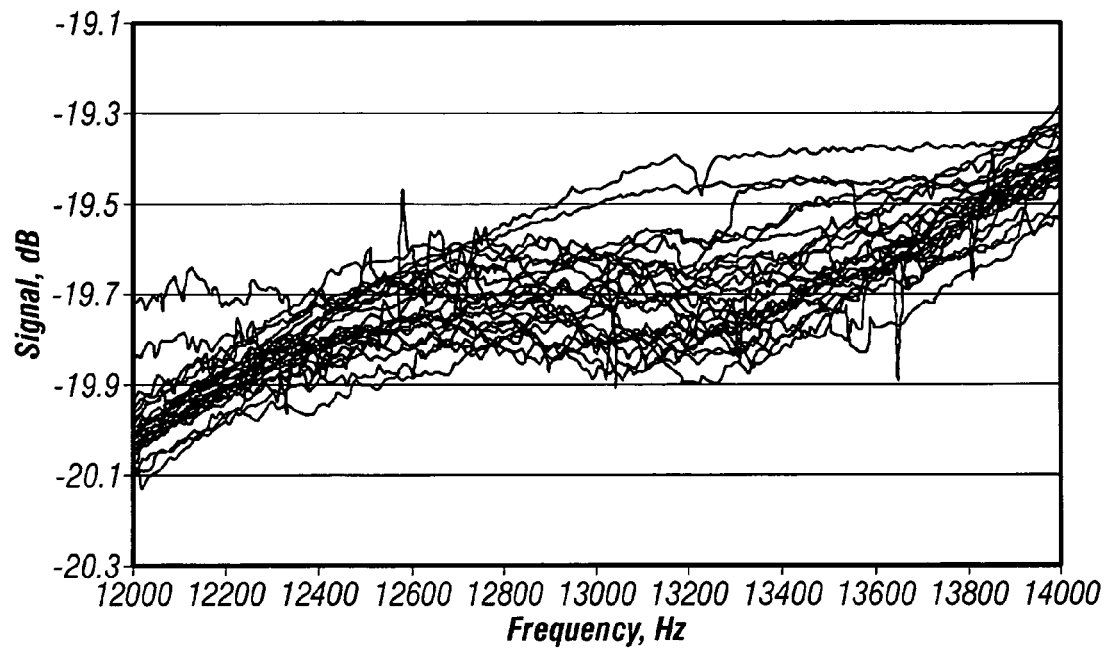
FIG. 13 is a chart reflecting 30 individual sensor frequency sweeps at 0.41 ft/s superficial gas velocity, 3 ft above the distributor plate in the 14" cold fluidized bed polymerization reactor model with HDPE.
Figure 14:
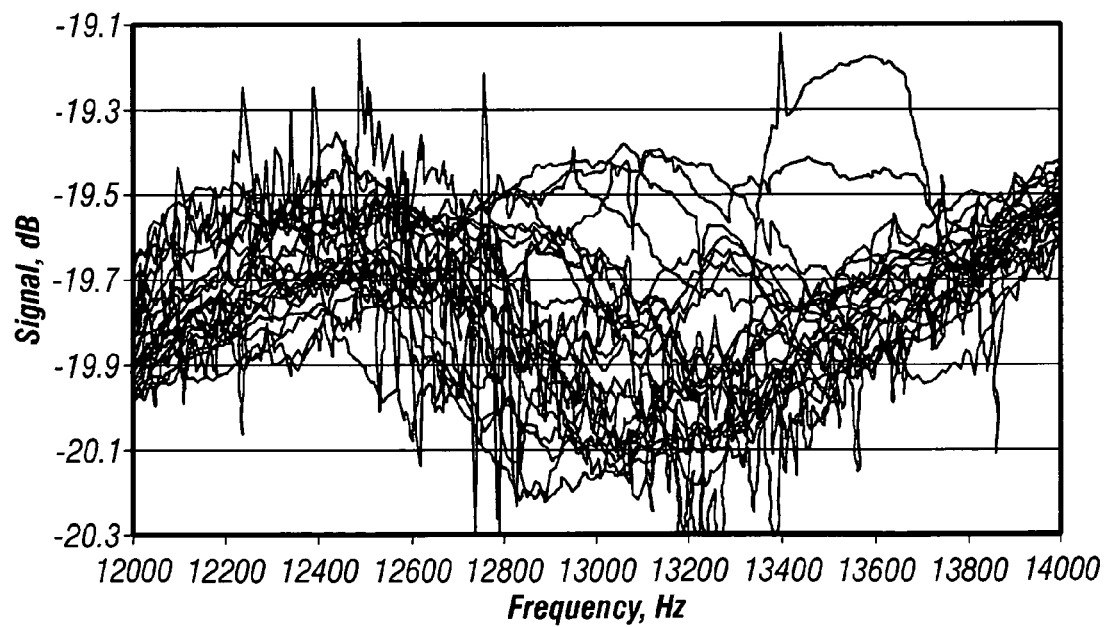
FIG. 14 is a chart reflecting 30 individual sensor frequency sweeps at 0.6 ft/s superficial gas velocity, 3 ft above the distributor plate in the 14" cold fluidized bed polymerization reactor model with HDPE.

The sensor signal-frequency curves shown in FIGS. 9 and 10 can be converted into a "localized density" factor which reflects the degree to which the bed absorbs energy from the fork. This can be done a number of different ways. In a particularly preferred embodiment, the electrical equivalence equations shown in FIG. 8B are used to calculate the effective impedance of the fork. In another embodiment, however, a simpler approach can be taken. As the bed absorbs more and more energy, the curve becomes more like a straight line. As such, one can simply sum the deviation of an actual average curve from the straight line between first and last points and it gives a quantitative measure of the peak-to-trough signal deflection, which is related to powder density. The simplified "localized density" factor for the upper port traces is shown as a function of SGV in FIG. 11.

The tuning fork sensor in active mode provides far more information about local fluidization than is evident from the averaged response curves described above. The local mixing, or mixing factor, is best characterized by the fluctuation in sensor response in time as mixing forces change the fluidization near the probe. This can be seen in FIGS. 12-14, which include a number of single frequency sweeps that were obtained over a period of ~300 ms each at intervals of about 2 seconds. Shown are the traces for the lowest velocities, which focus on the transition between fluidized and de-fluidized states; the corresponding curves at higher velocities show even greater differences. For reference, essentially no motion was visible at 0.3 ft/s SGV, while there was very gentle motion at 0.4 ft/s SGV, and some gentle bubbling at 0.6 ft/s SGV. It is clear from these plots that there are dramatic differences in the sensor response as the fluidized bed begins to move more vigorously. These differences are due to two contributing factors: variation in bed density around the probe, and possibly more significantly, energy transfer from the bed to the fork.

While it is visually obvious that the sensor is measuring differences in fluidization, a more thorough analysis of these data provides insight into the nature of those differences, and more importantly, can provide a useful way to present this data to a reactor operator. There are two principle components to the variation that becomes prevalent at the higher flows. The first is due to the density fluctuations that occur, and this appears as variation in peak-to-trough signal intensity from scan-to-scan. Such variation is visually evident in FIG. 13 at 0.4 ft/s where relatively smooth curves vary in intensity. The second component is more directly related to the particle motion, and appears as the jagged spikes (that look like noise) on the curves. The source of this jaggedness is as follows. Although the sensor is being driven into oscillations by the drive circuitry, particle/jet impacts also drive the fork into motion at levels that can exceed the driven oscillations in many cases. Such a spike occurs whenever in time a particle impacts the fork effectively, regardless of where the drive frequency is, and as such shows up as a positive or negative spike at any point in the trace.

Figure 15:
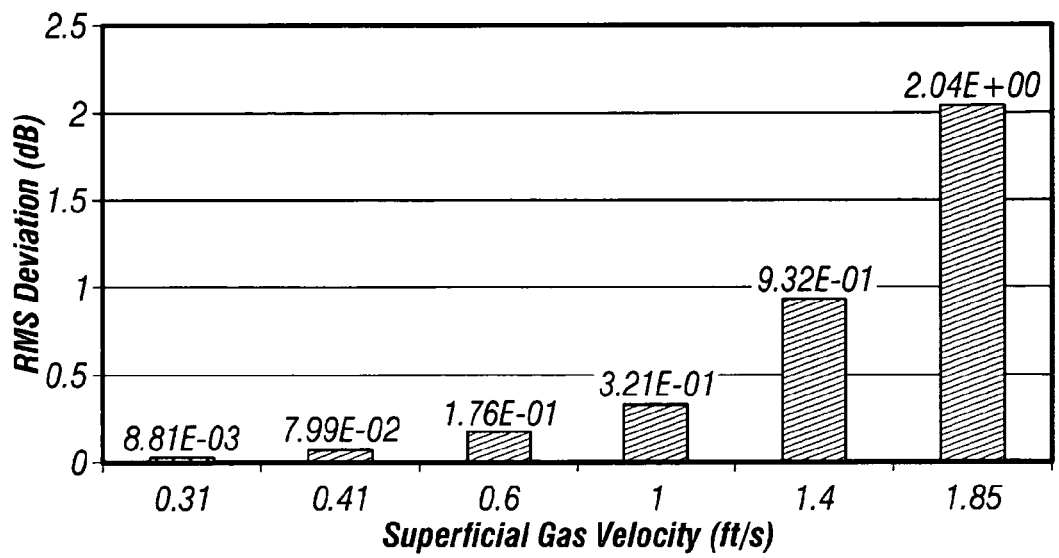
FIG. 15 is a chart reflecting Root-Mean-Square deviation representing a Mixing Factor vs. Superficial Gas Velocity three feet above the distributor plate in the 14" cold model with HPDE.
Figure 16:
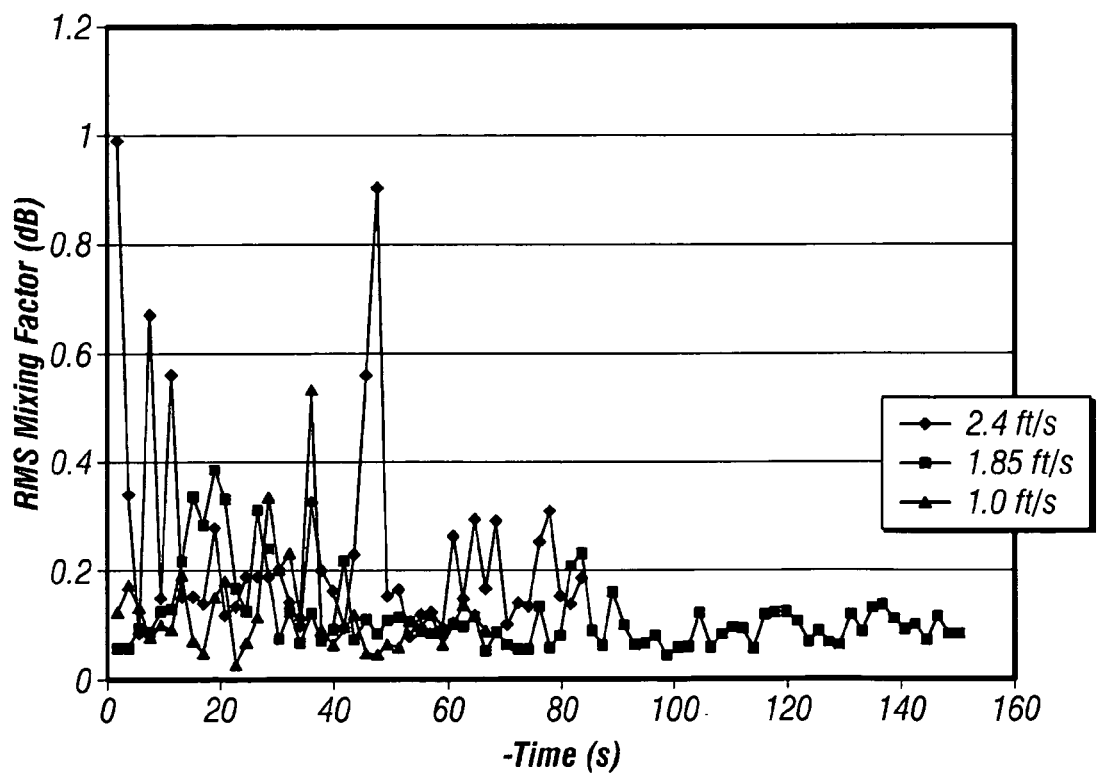
FIG. 16 is a chart reflecting a time series of the Root-Mean-Square deviation in a series of sensor scans relative to the moving average sensor signal, obtained from the 14" cold model with HDPE and with the tuning fork sensor ~1 ft above the distributor plate.

Analytically, there are a number of ways these variations can be quantified. A simple approach that measures the combined contribution of the two sources is to calculate the Root-Mean-Square (RMS) or standard deviation of the individual scans from the average curves that were shown in FIGS. 9 and 10. The more fluctuation, either from amplitude changes in smooth scans or spikes along a scan, the more standard deviation and therefore the more mixing that is occurring near the probe. The standard deviation for individual scans relative to average as a function of velocity is shown in FIG. 15. This standard deviation is one simple representation of a "mixing factor" in the fluidized bed near the probe.

This simple mathematical representation of the mixing factor contains contributions from both the slow density and velocity fluctuations as well as fast particle impacts as described above. Numerically, the contribution from an occasional particle impact can skew the total mixing factor toward higher values despite generally low velocity and density fluctuations and therefore periods of poor mixing. Accordingly, it can be useful to break down the mixing factor in terms of these two contributing factors to give the operator a more complete assessment of the type of mixing that is occurring.

Figure 17:
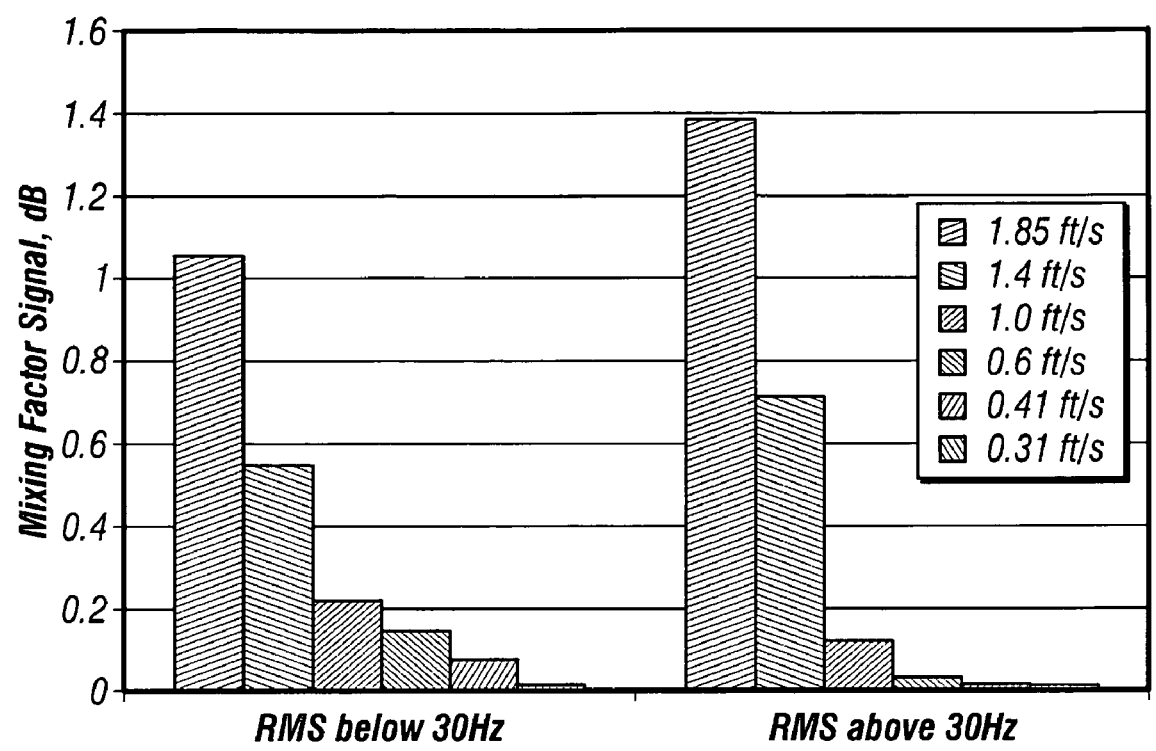
FIG. 17 is a chart reflecting slow (<30 Hz) and fast (>30 Hz) components of the Root-Mean-Square deviation representing a Mixing Factor as a function of superficial gas velocity, measured ~3 ft above the distributor plate in the 14" cold model with HDPE.

The relative contribution of particle impacts compared to density fluctuations can be determined by filtering the raw signal data in terms of its frequency components. The particle impacts manifest themselves as relatively high frequency events during the drive frequency sweeps, e.g., above about 30 Hz. The density fluctuations are known to occur over slower time scales, the fastest of which are on the order of 10 Hz. As such, by filtering the raw signal data using low- and high-pass filters with cut-offs of 30 Hz, one can evaluate the relative contributions of the two types of phenomena occurring in the bed. Such an analysis is shown in FIG. 17, which provides the RMS deviation "Mixing Factor" in terms of its slow (<30 Hz) and fast (>30 Hz) components. It is apparent from this plot that the mixing factor is dominated by the high frequency, particle-impact component at high SGV, but that that slow, gentle density fluctuations contribute the most to the mixing factor at low SGV. The fast component can be thought of as an indicator of the "granular temperature" of the fluidized bed. It is the slow component, however, that may provide the most direct warning to an approach to sheeting in the bed.

In light of the detailed description of the invention and the examples presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

We claim:

1. A method for monitoring fluidized polymer particles in a fluidized bed polymerization reactor system, the method comprising:
   polymerizing a gaseous monomer in a fluidized bed polymerization reactor of the system thereby forming fluidized polymer particles in the fluidized bed polymerization reactor,
   contacting a mechanical resonator with the fluidized polymer particles in the reactor system, and
   monitoring a response of the mechanical resonator to the contacting.

2. The method of claim 1 further comprising stimulating the mechanical resonator to generate the response of the mechanical resonator.

3. The method of claim 2 wherein the mechanical resonator is stimulated by the fluidized polymer particles impacting the mechanical resonator to generate a signal indicative of the response of the mechanical resonator.

4. The method of claim 2 wherein the mechanical resonator is stimulated by applying a variable frequency input signal to the mechanical resonator, and varying the frequency of the variable frequency input signal over a frequency range to generate a signal indicative of a frequency-dependent response of the mechanical resonator.

5. The method of claim 1 further comprising correlating the response of the mechanical resonator to a property of at least one of (i) the fluidized polymer particles, or (ii) a multi-phase system comprising the fluidized polymer particles.

6. The method of claim 1 wherein the mechanical resonator is a first mechanical resonator, the method further comprising impacting a second mechanical resonator with the fluidized particles, and monitoring a response of the second mechanical resonator.

7. The method of claim 1 further comprising determining a height of the fluidized bed in the fluidized bed reactor.

8. The method of claim 1 wherein the response of the mechanical resonator is monitored at multiple different times.

9. The method of claim 1 wherein the mechanical resonator contacts the polymer particles in the fluidized bed polymerization reactor.

10. The method of claim 1 wherein the mechanical resonator contacts the polymer particles in a portion of the system outside the fluidized bed polymerization reactor.

11. The method of claim 10 wherein the mechanical resonator contacts the polymer particles in a velocity reduction zone of the reactor of the fluidized bed polymerization reactor system.

12. The method of claim 10 wherein the mechanical resonator contacts the polymer particles in a recirculation subsystem of the fluidized bed polymerization reactor system.

13. The method of claim 1 wherein the fluidized bed polymerization reactor system includes a reactor having a reaction zone, a velocity reduction zone, and a transition portion positioned between the reaction zone and the velocity reduction zone, wherein the mechanical resonator is contacted with the fluidized polymer particles in the transition portion.

14. The method of claim 13 further comprising determining, based on the monitored response of the mechanical resonator, an extent that the fluidized polymer particles scrub the transition portion.

15. The method of claim 1 further comprising characterizing, in each case based on the monitored response of the mechanical resonator, the polymer particles by determining at least one of (i) a localized density, (ii) a granular temperature, (iii) a mixing factor, and (iv) an elastic modulus based on the monitored response of the mechanical resonator.

16. The method of claim 1 wherein the mechanical resonator is a flexural resonator.

17. The method of claim 1 wherein the mechanical resonator is a tuning fork resonator.

18. A method for monitoring a bed of polymer particles, the method comprising:
   contacting a mechanical resonator with polymer particles in the bed of polymer particles, the bed further comprising a gaseous fluid in interstitial spaces defined between the polymer particles,
   stimulating the mechanical resonator to generate a response of the mechanical resonator, and
   monitoring the response of the mechanical resonator to the contacting.

19. The method of claim 18 wherein the bed of polymer particles is a fluidized bed, wherein the mechanical resonator is stimulated by the polymer particles impacting the mechanical resonator to generate a signal indicative of the response of the mechanical resonator.

20. The method of claim 18 wherein the mechanical resonator is stimulated by applying a variable frequency input signal to the mechanical resonator, and varying the frequency of the variable frequency input signal over a frequency range to generate a signal indicative of a frequency-dependent response of the mechanical resonator.

21. The method of claim 18 wherein the mechanical resonator is a first mechanical resonator, the method further comprising impacting a second mechanical resonator with the particles, and monitoring a response of the second mechanical resonator.

22. The method of claim 18 wherein the response of the mechanical resonator is monitored at multiple different times.

23. The method of claim 18 wherein the bed of the polymer particles is at least one of a stagnant bed, a moving bed, a stirred bed, and a fluidized bed.

24. The method of claim 18 wherein the bed of polymer particles is positioned in a polymerization reactor system.

25. The method of claim 24 further comprising polymerizing a gaseous monomer in a fluidized bed polymerization reactor of the reactor system, thereby forming the polymer particles.

26. The method of claim 18 wherein the mechanical resonator is a flexural resonator.

27. The method of claim 18 wherein the mechanical resonator is a tuning fork resonator.

28. The method of claim 18 further comprising characterizing the particles by determining a particle-motion property based on the monitored response of the mechanical resonator.

29. A method for monitoring fluidized particles, the method comprising:
   fluidizing particles to form a multi-phase system comprising the fluidized particles and a gaseous continuous phase,
   contacting a mechanical resonator with the fluidized particles,
   stimulating the mechanical resonator to generate a response of the mechanical resonator,
   monitoring the response of the mechanical resonator to the contacting, and
   characterizing the multi-phase system by determining at least one of (i) a localized density, (ii) a granular temperature, (iii) a mixing factor and (iv) a particle-motion property of the particles in the multi-phase system, in each case based on the monitored response of the mechanical resonator.

30. The method of claim 29 wherein the mechanical resonator is stimulated by the fluidized particles impacting the mechanical resonator to generate a signal indicative of the response of the mechanical resonator.

31. The method of claim 29 wherein the mechanical resonator is stimulated by applying a variable frequency input signal to the mechanical resonator, and varying the frequency of the variable frequency input signal over a frequency range to generate a signal indicative of a frequency-dependent response of the mechanical resonator.

32. The method of claim 29 wherein the mechanical resonator is a first mechanical resonator, the method further comprising impacting a second mechanical resonator with the fluidized particles, and monitoring a response of the second mechanical resonator.

33. The method of claim 29 wherein the mechanical resonator is a first mechanical resonator, the method further comprising impacting a second mechanical resonator with the particles, and monitoring a response of the second mechanical resonator.

34. The method of claim 29 wherein the response of the mechanical resonator is monitored at multiple different times.

35. The method of claim 29 wherein the multi-phase system is maintained under a set of process conditions, the method further comprising varying at least one process condition based on a monitored output signal of the mechanical resonator.

36. The method of claim 29 wherein the at least one of (i) the localized density, (ii) the granular temperature, and (iii) the mixing factor are determined over the period of time, based on the monitored output signal of the sensor.

37. The method of claim 29 wherein the particles are polymer particles.

38. The method of claim 29 wherein the mechanical resonator is a flexural resonator.

39. The method of claim 29 wherein the mechanical resonator is a tuning fork resonator.

40. A method for determining an elastic modulus of particles in a multi-phase system, the method comprising:
   contacting a mechanical resonator with particles,
   stimulating the mechanical resonator to generate a response of the mechanical resonator,
   monitoring the response of the mechanical resonator, and
   determining an elastic modulus of the particles based on the monitored response of the mechanical resonator.

41. The method of claim 40 wherein the mechanical resonator is stimulated by the particles impacting the mechanical resonator to generate a signal indicative of the response of the mechanical resonator.

42. The method of claim 40 wherein the mechanical resonator is stimulated by applying a variable frequency input signal to the mechanical resonator, and varying the frequency of the variable frequency input signal over a frequency range to generate a signal indicative of a frequency-dependent response of the mechanical resonator.

43. The method of claim 40 wherein the mechanical resonator is a first mechanical resonator, the method further comprising stimulating a second mechanical resonator in contact with the particles. and monitoring a response of the second mechanical resonator.

44. The method of claim 40 wherein the response of the mechanical resonator is monitored at multiple different times.

45. The method of claim 40 wherein the particles are present in the form of a stagnant bed, a moving bed, or a fluidized bed.

46. The method of claim 40 wherein the particles are polymer particles positioned in a polymerization reactor system.

47. The method of claim 46 further comprising polymerizing a gaseous monomer in a fluidized bed polymerization reactor thereby forming the particles.

48. The method of claim 40 wherein the elastic modulus is determined over the period of time, based on the monitored output signal of the sensor.

49. The method of claim 40 wherein the mechanical resonator is a flexural resonator.

50. The method of claim 40 wherein the mechanical resonator is a tuning fork resonator.

51. A method for monitoring a polymerization reaction in a fluidized bed polymerization reactor system, the method comprising:
   polymerizing a gaseous monomer in a fluidized bed polymerization reactor of the system thereby forming fluidized polymer particles in the fluidized bed polymerization reactor,
   monitoring the fluidized polymer particles in the reactor system using a sensor comprising a mechanical resonator, and
   determining, based on a monitored response of the sensor to contact of the mechanical resonator with the polymer particles, at least one of (i) an occurrence or extent of agglomeration of the fluidized polymer particles in the system, (ii) an occurrence or extent of polymer sheeting in the system, (iii) a rate of polymerizing in the fluidized bed polymerization reactor, (iv) a level of condensed liquid in the fluidized bed polymerization reactor, (v) an occurrence or extent of channeling of the fluidized polymer particles in the system, (vi) an occurrence or extent of fluidization of the polymer particles in the system, and (vii) an occurrence or extent of plugging of a gas distribution plate in the system.

52. The method of claim 51 wherein the mechanical resonator is stimulated by applying a variable frequency input signal to the mechanical resonator, and varying the frequency of the variable frequency input signal over a frequency range to generate a signal indicative of a frequency-dependent response of the mechanical resonator.

53. The method of claim 51 wherein the mechanical resonator is a flexural resonator.

54. The method of claim 51 wherein the mechanical resonator is a tuning fork resonator.

55. A method for controlling a process condition in a fluidized bed polymerization reactor system, the method comprising:
  polymerizing a gaseous monomer in a fluidized bed polymerization reactor of the system under a set of process conditions to form fluidized polymer particles in the reactor,
  monitoring a response of a sensor caused by contact of the sensor with the polymer particles in the fluidized bed polymerization reactor system over a period of time, wherein the sensor comprises a mechanical resonator, and
  varying at least one process condition of the set based on a monitored output signal of the sensor.

56. The method of claim 55 wherein the mechanical resonator is stimulated by applying a variable frequency input signal to the mechanical resonator, and varying the frequency of the variable frequency input signal over a frequency range to generate a signal indicative of a frequency-dependent response of the mechanical resonator.

57. The method of claim 55 further comprising characterizing a property of at least one of (i) the fluidized polymer particles or (ii) a multi-phase system comprising the fluidized polymer particles, over the period of time, based on the monitored output signal of the sensor.

58. The method of claim 55 wherein said at least one process condition comprises varying a flow rate of the fluidizing gas into the fluidized bed polymerization reactor.

59. The method of claim 55 wherein the at least one process condition is selected from the group consisting of (i) a flow rate of the gaseous monomer into the fluidized bed polymerization reactor, (ii) a rate of heat removal from the fluidized bed polymerization reactor, and (iii) combinations thereof 60. The method of claim 55 wherein the at least one process condition is selected from the group consisting of (i) a catalyst feed rate, (ii) a recycle gas flow rate, (iii) a gas composition, (iv) a static control agent flow rate, and (v) a sheeting control agent flow rate, and (vi) combinations thereof.

61. A system comprising a fluidized bed polymerization reactor system, the fluidized bed polymerization reactor system comprising:
  a reactor vessel having an inlet port, the inlet port being adapted for receiving a gaseous fluid for fluidizing polymer particles in the reactor vessel, and
  a sensor comprising a mechanical resonator, the mechanical resonator comprising a sensing surface adapted for exposure to the fluidized polymer particles within the reactor system, wherein a response of the sensor is indicative of impacts of the fluidized polymer particles against the sensing surface.

62. The system of claim 61 further comprising a catalyst inlet port in the reactor vessel for providing catalyst into the reaction vessel.

63. The system of claim 61 further comprising a fluid outlet port, the fluid outlet port being adapted for discharging a gaseous fluid from the reactor vessel.

64. The system of claim 61, further comprising a polymer particle discharge port positioned in the lower portion of the reactor vessel for discharging the polymer particles from the reactor vessel.

65. The system of claim 61, wherein the sensor is positioned in a reaction zone of the reaction vessel.

66. The system of claim 61, wherein the sensor is positioned in a velocity reduction zone of the reaction vessel.

67. The system of claim 61, wherein the reactor vessel includes a reaction zone, a velocity reduction zone, and a transition portion positioned between the reaction zone and the velocity reduction zone, wherein the mechanical resonator is positioned in the transition portion.

68. The system of claim 61, wherein the sensor is positioned in a recirculation subsystem of the reactor system.

69. The system of claim 61, further comprising a signal processing circuit in electrical communication with the mechanical resonator for receiving an output signal from the mechanical resonator during a sensing period, the signal processing circuit configured for processing the received signal to generate data indicative of the response of the mechanical resonator, and a data retrieval circuit for monitoring the generated data.

70. An apparatus comprising a sensor for use in monitoring fluidized particles, the sensor comprising:
  a flexural resonator having a sensing surface adapted for exposure to a multi-phase system comprising fluidized particles in at least one of a gaseous continuous phase and a liquid phase, and
  a signal processing circuit in electrical communication with the flexural resonator for receiving an output signal from the flexural resonator during a sensing period, the signal processing circuit configured for processing the received signal to generate data representing at least one of localized density of the fluidized particles, granular temperature of the fluidized particles, mixing factor of the fluidized particles and combinations thereof.

71. The apparatus of claim 70 wherein the signal processing circuit comprises a processor configured for fitting the received signal to an equation representing an equivalent circuit, the equivalent circuit modeling a property of the fluidized particles or of a multi-phase system comprising the fluidized particles in a gaseous continuous phase.

72. The apparatus of claim 70 wherein the signal processing circuit comprises a processor configured for fitting the received signal to an equation representing an equivalent circuit, the equivalent circuit modeling the localized density of the fluidized particles in the multi-phase system.

73. The apparatus of claim 70 wherein the signal processing circuit comprises a processor configured for fitting the received signal to an equation representing an equivalent circuit, the equivalent circuit modeling the granular temperature of the fluidized particles in the multi-phase system.

74. The apparatus of claim 70 wherein the signal processing circuit comprises a processor configured for fitting the received signal to an equation representing an equivalent circuit, the equivalent circuit modeling the mixing factor of the fluidized particles in the multi-phase system.

75. The apparatus of claim 70 further comprising a circuit for providing an excitation signal for stimulating the flexural resonator.

76. The apparatus of claim 70 further comprising a circuit for generating a visual output from the data representing the property of the multi-phase system.

77. In a fluidized bed polymerization reaction system comprising a reaction vessel, the improvement comprising:
  a sensor comprising a mechanical resonator, the mechanical resonator comprising a sensing surface adapted for exposure to the fluidized polymer particles within the reactor system, wherein a response of the sensor is indicative of impacts of the fluidized polymer particles against the sensing surface.

* * * * *

UNITED STATES PATENT AND TRADEMARK OFFICE
CERTIFICATE OF CORRECTION

| | |
|---|---|
| PATENT NO. | : 7,634,937 B2 |
| APPLICATION NO. | : 11/296597 |
| DATED | : December 22, 2009 |
| INVENTOR(S) | : Burdett et al. |

It is certified that error appears in the above-identified patent and that said Letters Patent is hereby corrected as shown below:

col. 15, line 66 insert --For-- before "a" and after "Analysis";
col. 35, line 11 replace "14'" with --14"--.

Signed and Sealed this

Sixteenth Day of February, 2010

David J. Kappos
*Director of the United States Patent and Trademark Office*